United States Patent
Patterson et al.

(10) Patent No.: US 7,557,215 B2
(45) Date of Patent: Jul. 7, 2009

(54) ANTHRAQUINONE COMPOUNDS AS ANTI CANCER COMPOUNDS

(75) Inventors: Laurence Hylton Patterson, West Yorkshire (GB); Klaus Pors, West Yorkshire (GB); Paul Henry Teesdale-Spittle, Wellington (NZ)

(73) Assignee: Somanta Limited, London (GB)

( * ) Notice: Subject to any disclaimer, the term of this patent is extended or adjusted under 35 U.S.C. 154(b) by 46 days.

(21) Appl. No.: 10/596,783

(22) PCT Filed: Dec. 22, 2004

(86) PCT No.: PCT/GB2004/005390

§ 371 (c)(1),
(2), (4) Date: Feb. 8, 2007

(87) PCT Pub. No.: WO2005/061453

PCT Pub. Date: Jul. 7, 2005

(65) Prior Publication Data

US 2008/0027107 A1   Jan. 31, 2008

(30) Foreign Application Priority Data

Dec. 23, 2003 (GB) ................................. 0329820.5
Dec. 24, 2003 (GB) ................................. 0330011.8

(51) Int. Cl.
*C07D 211/00* (2006.01)
*C07D 207/04* (2006.01)
(52) U.S. Cl. ..................................... 546/246; 548/569
(58) Field of Classification Search ................ 546/204, 546/246; 548/528, 569
See application file for complete search history.

(56) References Cited

OTHER PUBLICATIONS

Murdock et al. Journal of Medicinal Chemistry (1979), 22(9), 1024-30.*
Collier et al. Journal of Medicinal Chemistry (1988), 31(4), 847-857.*
Agbandje et al. Journal of Medicinal Chemistry (1992), 35(8), 1418-1429.*

* cited by examiner

*Primary Examiner*—D. Margaret Seaman
*Assistant Examiner*—Nizal S Chandrakumar
(74) *Attorney, Agent, or Firm*—Whitham Curtis Christofferson & Cook, P.C.

(57) ABSTRACT

Anthraquinone compounds of the general formula (I) or a salt thereof (Formula I) in which $R^1$ to $R^4$ are each selected from the group consisting of H, $C_{1-4}$ alkyl, $X^1$, —$NHR^0N(R^5)_2$ in which $R^0$ is a $C_{1-12}$ alkanediyl and each $R^5$ is H or optionally substituted $C_{1-4}$ alkyl, and a group of formula (II) in which at least one of $R^6$, $R^7$ and $R^8$ is selected from $X^2$, and $X^2$ substituted $C_{1-4}$ alkyl and any others are H or $C_{1-4}$ alkyl; $R^9$ is selected from H, $C_{1-4}$ alkyl, $X^2$ and $X^2$ substituted $C_{1-4}$ alkyl; m is 0 or 1; n is 1 or 2; $X^1$ is a halogen atom, a hydroxyl group, a $C_{1-6}$ alkoxyl group, an aryloxy group or an acyloxy group; and $X^2$ is a halogen atom, a hydroxyl group, a $C_{1-6}$ alkoxyl group, an aryloxy group or an acyloxy group; provided that at least one of $R^1$ to $R^4$ is a group of formula (II). The N-oxides are useful prodrugs which are selectively bioreduced in hypoxic tumours to the corresponding cyclic amine derivatives. The amine compounds are cytotoxic and may be used as alkylating agents having topoisomerase II inhibiting activities in cancer therapy.

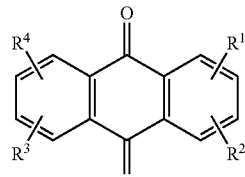

(I)

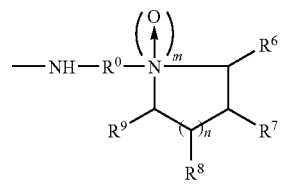

(II)

24 Claims, 4 Drawing Sheets

Scheme 2

Scheme 3

Scheme 4

Scheme 5

ANTHRAQUINONE COMPOUNDS AS ANTI CANCER COMPOUNDS

The present invention relates to a series of substituted alkylaminoanthraquinones, with nitrogen containing heterocyclic substituents, as well as N-oxides of these compounds. The compounds may be alkylating agents having topoisomerase II inhibiting activities. The N-oxides are prodrugs.

Resistance to antitumour drugs is the main cause for the failure of cancer chemotherapy and a number of mechanisms for resistance are known. For example loss of DNA mismatch repair with in vitro models leads to resistance to a number of clinically important antitumour agents, including cisplatin and doxorubicin, and has been demonstrated to correlate with hypermethylation of the hMLH1 gene promoter region. One approach to the reversal of this mechanism of drug resistance is through treatment with a demethylating agent, which then reinstates the sensitivity of the cell lines to classical antitumour agents. Treatment of human tumour xenografts of the cisplatin resistant variant of the A2780 ovarian tumour cell line (A2780/cp70) with the demethylating agent 2'-deoxy-5-azacytidine led to sensitization to various antitumour agents. However, it may also be possible to exploit differences in the resistant and non-resistant cell lines that allow treatment with antitumour agents that are more effective against the resistant cell lines.

Over the past 25 years, there have been extensive investigations on non-covalent DNA binding 1,4-disubstituted aminoanthraquinones. Most of this research has concerned symmetrically substituted agents such as mitoxantrone, a clinically utilised analogue of the anthracycline antibiotics, and AQ4N, Patterson L. H. Drug Metabolism Reviews, 2002, 34, 581-92 and WO-A-9105824 a bioreductively activated agent that is currently undergoing Phase I clinical trials.

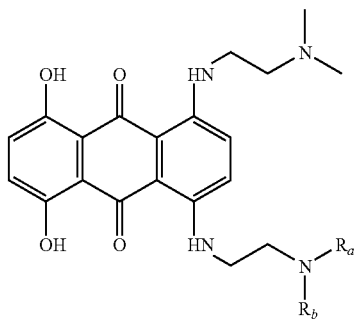

AQ6 $R_a$ = H, $R_b$ = $CH_2CH_2OH$
ZP257 $R_a$ = $CH_3$, $R_b$ = $CH_2CH_2OH$
ZP275 $R_a$ = $R_b$ $CH_2CH_2OH$
Alchemix $R_a$ = $R_b$ = $CH_2CH_2Cl$ AQ6 is a non-symmetrically substituted aminoanthraquinone that was developed by Patterson and co-workers, WO-A-9105824 and Smith P. J.; Blunt N. J.; Desnoyers R.; Giles Y.; Patterson L H. Cancer Chemotherapy and Pharmacology, 1997, 39, 455-461 and reported on by Krapcho et al. Journal of Medicinal Chemistry, 1991, 34, 2373-2380. Patterson showed that AQ6 inhibits kinetoplast DNA decatenation with enhanced cytotoxic potential under conditions of overexpression of topoisomerase II. In addition, Krapcho et al. showed it to have excellent in vitro cytotoxicity in a colon carcinoma doxorubicin-resistant cell line, and moderate activity in L1210 cells in vivo.

In a recent study on novel aminoanthraquinones, we observed that two non-symmetrical aminoanthraquinones, ZP257 and ZP275, had considerable cytotoxic activity in a panel of ovarian cancer cell lines. Pors K, Paniwnyk Z. Teesdale-Spittle P, Plumb J A, Willmore E, Austin C A, Patterson L H. (2003) *Alchemix: A Novel Alkylating Anthraquinone with Potent Activity against Anthracycline- and Cisplatin-resistant Ovarian Cancer. Mol Cancer Ther.* 2(7): 607-610. ZP257 and ZP275 were shown to be cross-resistant with doxorubicin in a P-glycoprotein over expressed cell line (2780AD) but were significantly more active in the cisplatin resistance, A2780/cp70, cell line compared to the wildtype. AQ6, ZP257 and ZP275 are analogues of mitoxantrone in which one of the two hydroxyethylaminoethyl side chains is replaced by a N,N-dimethylaminoethyl side chain or N-methyl-N-hydroxyethylaminoethyl side chain. These two agents have high but equal cytotoxic activity against both the A2780 and A2780/cp70 cell lines, (i.e. a resistance factor (RF) of approx. 1).

Alchemix, one of the compounds described by Pors et al, is an alkylating agent, by virtue of being a mustard derivative. In Alchemix, the two N substituents in one of the aminoalkylamino sidechains are 2-chloroethyl. A number of other mustard compounds are described in that reference.

The A2780/cp70 cell line is deficient in DNA mismatch repair (MMR) proteins including hMLH1 and hMSH2, and it has been shown previously that loss of either is associated with resistance to topoisomerase II inhibitors such as doxorubicin, epirubicin and mitoxantrone. Fedier A.; Schwarz V. A.; Walt H., Carpini R. D.; Haller U.; Fink D. International Journal of Cancer, 2001, 93, 571-576.

N-oxides of some classes of DNA interacting agents are known to be inactive until bioreduced in hypoxic tissue (Patterson L. H. and Mckeown S. R., Brit J Cancer 2000 83(12), 1589-93). A4QN is an example of such N-oxides. The value of N-oxides of DNA binding cytotoxic agents is that they are selectively activated in hypoxic tumour tissue to potent cytotoxins. Conventional chemotherapy and radiation therapy will preferentially kill tumour tissue that is well perfused with oxygenated blood. Hypoxic tumour tissues are poorly perfused and have low oxygen and hence are refractory to conventional therapy. Bioreductive agents are preferentially reduced to active cytotoxins in hypoxic tumour tissue and exert cell killing that contributes to the total therapeutic effect when given in combination with radiotherapy or cytotoxic agents.

We attempted to synthesise the corresponding N-oxides of the compounds in Pors et al, however the oxidised compounds were unstable, and proved difficult or impossible to isolate. It would be desirable to produce prodrugs having the advantages of the mustard compounds described by Pors et al, which would be selectively bioreduced in tumours, as well as precursors thereof.

In WO-A-9105824 the amino alkyl amino substituent could include a cyclic N-containing group, but the alkane diyl group joined to the nitrogen atom was not substituted.

According to the present invention there is provided a novel anthraquinone compound of the general formula I or a salt thereof

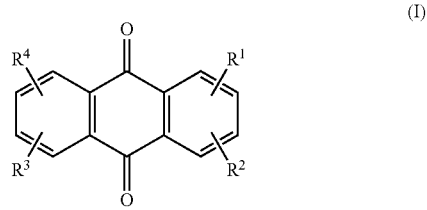

(I)

in which $R^1$ to $R^4$ are each selected from the group consisting of H, $C_{1-4}$ alkyl, $X^1$, —$NHR^0N(R^5)_2$ in which $R^0$ is a $C_{1-12}$ alkanediyl and each $R^5$ is H or optionally substituted $C_{1-4}$ alkyl, and a group of formula II

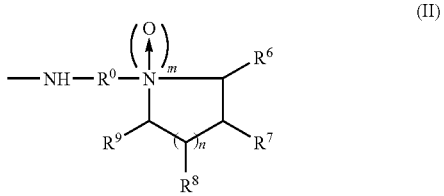

(II)

in which at least one of $R^6$, $R^7$ and $R^8$ is selected from $X^2$, and $X^2$ substituted $C_{1-4}$ alkyl and any others are H or $C_{1-4}$ alkyl; $R^9$ is selected from H, $C_{1-4}$ alkyl, $X^2$ and $X^2$ substituted $C_{1-4}$-alkyl;

m is 0 or 1;

n is 1 or 2;

$X^1$ is a halogen atom, a hydroxyl group, a $C_{1-6}$ alkoxyl group, an aryloxy group or an acyloxy group; and $X^2$ is a halogen atom, a leaving group, a hydroxyl group, a $C_{1-6}$ alkoxyl group, an aryloxy group or an acyloxy group;

provided that at least one of $R^1$ to $R^4$ is a group of formula II.

In the invention, $R^1$ and $R^2$ may each be a group of formula II. Although they may represent different groups of the formula II, generally the compound is symmetrical, and the groups $R^1$ and $R^2$ would be the same as one another.

Preferably, however, $R^1$ and $R^2$ are not identical, but rather represent different moieties. Such non-symmetric compounds have the advantage of providing enhanced activity against cisplatin resistant cancer cells. Preferably $R^1$ is a group of formula II and $R^2$ is a group $NHR^0N(R^5)_2$. In such groups $R^2$, the groups $R^5$ are preferably the same as one another and are generally hydrogen or methyl.

Where each of $R^1$ and $R^2$ is an aminoalkylamine moiety, they are preferably substituted at the 1 and 4 positions, respectively, on the anthraquinone ring system. The numbering convention in the anthraquinone ring system is as follows:

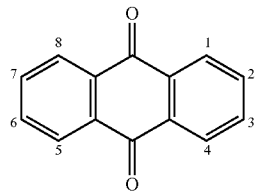

The groups $R^3$ and $R^4$ may each represent one of the aminoalkylamine groups, that is a group of general formula II or a group $NHR^0N(R^5)_2$. Preferably, however, $R^3$ and $R^4$ are selected from hydrogen and hydroxyl and are preferably both the same. $R^3$ and $R^4$ are preferably located at positions 5 and 8, respectively, in the anthraquinone ring system. In one group of compounds of the invention, $R^3$ and $R^4$ are both hydrogen. In another group of compounds, $R^3$ and $R^4$ are both hydroxyl.

In the invention, the compound may be in the form of the N-oxide, that is in which m is 1. Alternatively the compounds may be in the non-oxidised (or reduced) form, in which m is 0. The N-oxides are useful prodrugs which are selectively bioreduced in hypoxic tumours to the corresponding amine.

The amine compounds are cytotoxic compounds. They may be useful in cancer therapy as such, and accordingly the present invention provides the use of the amine in the manufacture of a medicament for use in the treatment of an animal. The invention further provides the use of the N-oxides in the manufacture of medicaments for use in the treatment of an animal. The compounds may be present as racemic mixtures or as isolated R- or S- enantiomers (i.e. in which the cyclic heteryl group has its side chains in selected orientation) vis-a-vis the link from the nitrogen atom.

The compounds of the present invention may be pyrrolidine derivatives, that is in which n is 1. Another class of compounds of the invention are piperidine derivatives, in which n is 2.

One preferred class of compounds of the invention are alkylating agents. In such compounds, either i) $R^6$ is $CH_2X^2$ and $R^7$ is H; or ii) $R^6$ is H and $R^7$ is $X^2$, and wherein $X^3$ is a halogen atom or a leaving group. Alternatively or additionally, $R^6$ is $CH_2CH_2X^3$. Where $R^6$ is $CH_2X^3$, $R^9$ may conveniently be the same group.

Suitable examples of halogen atoms as $X^1$, $X^2$ or $X^3$ are fluorine, chlorine, bromine and iodine, preferably chlorine. Suitable examples of leaving groups as $X^1$, $X^2$ or $X^3$ are (i.e. nucleofugal groups) are alkyl aryl sulphonates, acyloxy or aryloxy groups.

$R^0$ is preferably $C_{2-6}$ alkanediyl, preferably a linear alkanediyl, group.

Compounds in which the groups $R^6$ and $R^7$ are not one of the definitions mentioned above in connection with alkylating agents, may nevertheless be DNA binding agents which act as topoisomerase II inhibitors. Compounds in which one of $R^6$, $R^7$ or $R^8$ is a hydroxyl group or a hydroxyalkyl group have cytotoxic properties. Halogen substituted compounds additionally are cytotoxic, even if they do not have halogen located in a position such that the compound is an alkylating agent (mustard).

The methods for synthesising the compounds are generally conventional. Preferably the compounds are made by producing a precursor cyclicamino alkylamine and reacting this in a nucleophilic substitution with an appropriately substituted anthraquinone compound. Suitably the substituent is a halogen atom, or another leaving group. Where there are two aminoalkylamine groups, these may be added by successive steps or, if a mixed product is acceptable, may be produced using a mixture of aminoalkylamines.

According to the invention there is provided a method in which a compound of the formula III

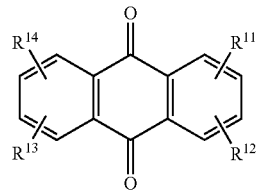

(III)

in which $R^{11}$ to $R^{14}$ are each selected from H, $X^4$, hydroxyl, $C_{1-4}$ alkoxy, acyloxy, a group —$NHR^{10}N(R^{15})_2$ in which $R^{10}$ is $C_{1-12}$ alkane diyl and each $R^{15}$ is H or optionally substituted $C_{1-4}$ alkyl, and in which $X^4$ is a halogen atom or a leaving group provided that at least one of $R^{11}$ to $R^{14}$ is $X^4$;

is reacted with a cyclic aminoalkylamine compound of the general formula IV

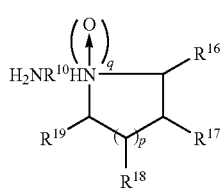

(IV)

such that the group $X^4$ is replaced in a nucleophilic substitution reaction by a group of formula V

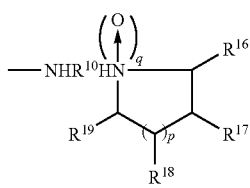

(V)

in which either at least one of $R^{16}$, $R^{17}$ and $R^{18}$ is selected from $X^5$ and $X^5$ substituted $C_{1-4}$ alkyl and any others are H or $C_{1-4}$ alkyl, and $R^{19}$ is selected from H, $C_{1-4}$ alkyl, $X^5$ and $X^5$ substituted $C_{1-4}$ alkyl;

$X^5$ is hydroxyl or a protected hydroxyl, or $X^5$ is a leaving group or a halogen atom different to $X^4$.

In the method, the groups $R^{16}$, $R^{17}$, $R^{18}$ and $R^{19}$ may be the same as in the desired end product of the general formula I as the groups $R^6$, $R^7$, $R^8$ and $R^9$, as the case may be. Alternatively, these groups may be precursors for the desired end groups and may be reacted in a subsequent reaction step to generate the desired substituents $R^6$ to $R^9$. Examples of subsequent reaction steps would be halogenating steps, carried out on hydroxyl or, protected hydroxyl, after deprotection, groups. In such processes, a group $X^5$ which is a hydroxyl or a protected hydroxyl group is reacted with a halogenating agent such as a chlorinating agent, optionally after deprotection, to replace the or each $X^5$ hydroxyl group by a halogen atom.

Where the desired end product is a N-oxide, that is where m is 1 and where q=0, the product of the nucleophilic substitution reaction is oxidised at the ring nitrogen atom to form the corresponding amine oxide. Oxidation is carried out using conventional oxidising agents, such as Chloroperoxybenzoic acid (m-CPBA), oxaziridine or Dimethyldioxirine (DMD).

Where the desired end product is an non-symmetrically substituted anthraquinone, that is in which one of the groups $R^1$ to $R^4$ is a group $NHR^0N(R^5)_2$, this compound is reacted in a preliminary nucleophilic substitution reaction, preferably in a preliminary step. In the preliminary step, a precursor of compound III, in which the group corresponding to $R^{11}$ to $R^{14}$ which is to be substituted having a substituent $X^6$ which is a halogen atom or a leaving group, is reacted with an amine $H_2NR^{10}N(R^{15})_2$ in which $R^{15}$ is H or an optionally substituted $C_{1-4}$ alkyl group. For instance, $R^{11}$ may be the leaving group $X^5$ and be at the one position in the anthraquinone ring system. $R^{12}$ in the compound of formula III may be the said acyclic alkyl amino alkyl group, and the precursor group is a leaving group $X^6$ and be at the one position in the anthraquinone ring system. $R^{12}$ in the compound of formula III may be the said acyclic alkyl amino alkyl group, and the precursor group is a leaving group $X^6$, and in the preliminary step, the group $X^6$ is replaced by the group $—NHR^{10}N(R^{15})_2$.

In the method, the cyclic amino alkyl amines are commercially available or may be synthesised in preliminary steps. A variety of examples of such starting compounds and their synthesis is described in the worked examples below. Some of the cyclic amino alkylamines are new.

According to a further aspect of the invention there is provided a compound of the general formula VII

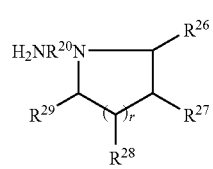

(VII)

in which $R^{20}$ is a $C_{1-12}$-alkanediyl group and either $R^{26}$ is $CH_2Cl$, and $R^{27}$ is H, or $R^{26}$ is H and $R^{27}$ is Cl;.

$R^{29}$ is H or is the same group as $R^{26}$;

the or each $R^{28}$ is H or is the same group as $R^{27}$; and r is 1 or 2.

Preferably $R^{20}$ is $(CH_2)_2$.

In one class of compounds VII r is 1. In another class r is 2. $R^{29}$ may be the same as $R^{26}$, but is often H.

The novel cyclic amines are made in a preliminary synthetic method in which a hydroxyl-substituted cyclic tertiary amine of the general formula VIII

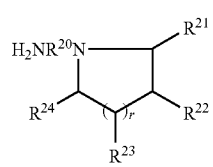

(VIII)

in which $R^{20}$ and r are as defined for compound VII either $R^{21}$ is $CH_2OH$ and $R^{22}$ is H or $R^{21}$ is H and $R^{22}$ is OH;

$R^{24}$ is H or is the same group as $R^{21}$;

the or each $R^{23}$ is H or is the same group as $R^{22}$;

is amine group protected, is then chlorinated by a process in which the OH is replaced by Cl, and is deprotected to afford the desired compound of formula VII.

The novel cyclic amines may be useful starting materials for derivatising other drugs and converting them to mustard derivatives.

Where the desired end product is a symmetrically substituted compound, with two cyclic amino alkyl amine substituents, the compound of the formula III will be a compound in which $R^{11}$ and $R^{12}$ represent $X^4$, both being the same group, and in the reaction, two equivalents of the amine compound of the general formula IV are reacted with one equivalent of the compound of the formula III.

The N-oxides of the present invention are useful prodrugs. They are reduced in hypoxic tumour tissue to the active cyclic amine derivative. They may be used in conjunction with the administration of related cytotoxic or entirely different cytotoxic agents, so as to contribute to the total therapeutic effect. Alternatively, the cyclic amine compound may be administered as such as a cytotoxic agent, with or without additionally targeting to the site of intended activity. The cytotoxic properties, and the generation of active cytotoxic agent from N-oxide prodrug, is demonstrated in the in vitro experiments in the examples below. From the results it would be reasonable to expect a useful in vivo activity as a cytotoxic agent, specifically for use in tumour therapy.

EXAMPLES

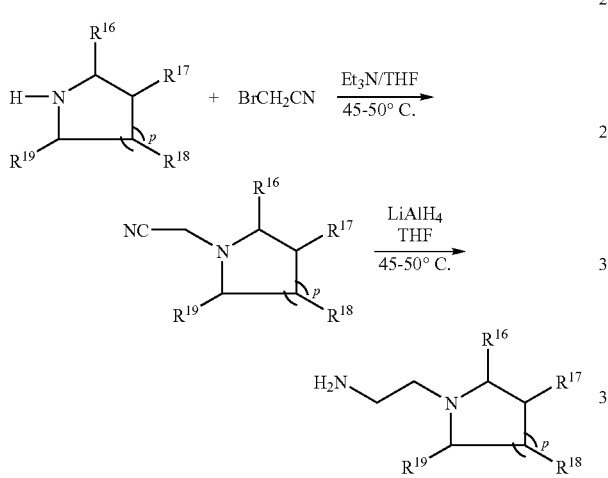

Scheme 1

General Method 1

Synthesis of the Aminoalkylamino Sidechains—General Method

Synthesis of the 1-(2-aminoethyl)pyrrolidine and piperidine side chains was a two-step procedure. The cyclic secondary amine was alkylated by bromoacetonitrile (dry Et$_3$N, THF, 45-50° C., 30 min, yield 63-92%) and the nitrile was converted to a primary amine by reduction with LiAlH$_4$ (THF, reflux, 5 h, yield 27-76%). The general method is used for 2-, 3- and 4-hydroxyl piperidines, 2- and 3-hydroxyl pyrrolidines and 2- and 6-bishydroxy-methyl piperidines.

General Method 2 —Synthesis of Aminoanthraquinones

Figure 1:
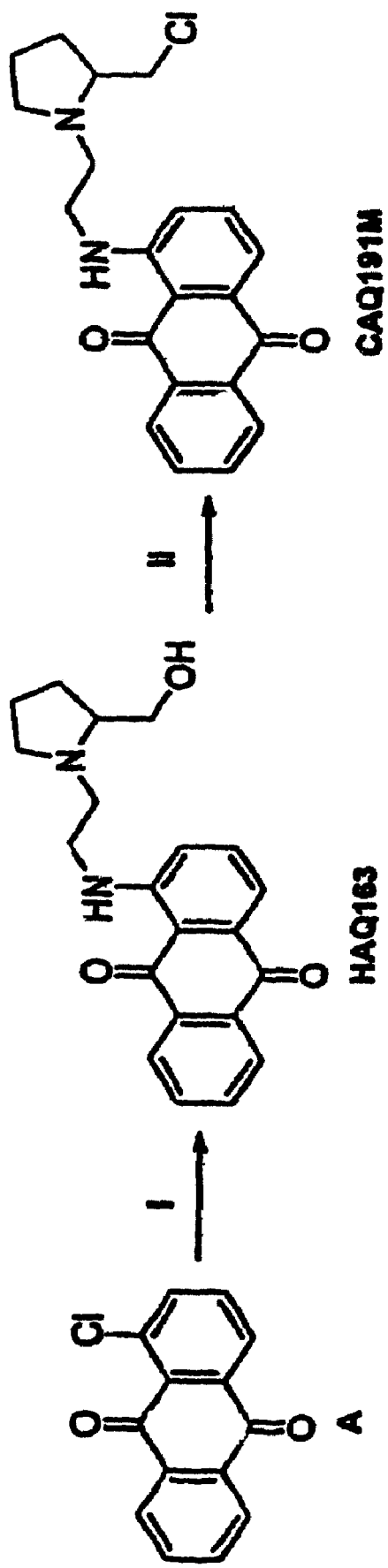
FIG. 1 is a reaction scheme referred to herein as Scheme 2.

Treatment of 1,4-difluoro-5,8-dihydroxyanthraquinone with N,N-dimethylethylenediamine led to a mixture of the di- and monosubstituted anthraquinones from which the intermediate HAQ107 was isolated by flash chromatography (N,N-dimethylethylenediamine, C$_5$H$_5$N, 22° C., 24 h, 34%) (Scheme 2, FIG. 1). Pure HAQ107 was then treated with the piperidine or pyrrolidine sidechains to afford the target compounds (HAQ71, HAQ73, HAQ110, HAQ111 and HAQ121) and the non-hydroxylated analogue HAQ148 in good yield after purification (Amine, C$_5$H$_5$N, 90° C., 30 min –1 h, 51-65%). HAQ70 and HAQ105, the symmetrically configured anthraquinones, were synthesised in one step by ipso-substitution of both fluoro groups of C with 1-(2-aminoethyl)-piperidine sidechains (C$_5$H$_5$N, 90° C., 1 h, 34-37%) (Scheme 3, FIG. 2). Preparation of the chloropropylaminoanthraquinones CAQ74 and CAQ75 were carried out by treating the precursor alcohols (HAQ70 and HAQ71 respectively) with triphenylphosphine-carbon tetrachloride, a commonly employed, complex reagent for conversion of alcohols to corresponding halides (Ph$_3$P, CCl$_4$, CH$_2$Cl$_2$, reflux, N$_2$, 5 h, 68-81%).

Synthesis of Hydroxylated N-Acetonitrile-Piperidines and Pyrrolidines

Reference Example 1

3-Hydroxy-piperidin-1-yl-acetonitrile (S1)

BrCH$_2$CN (3.19 g, 25.82 mmol) was added dropwise to a solution of 3-hydroxypiperidine (6.53 g, 64.55 mmol) in dry THF (25 mL) under N$_2$, maintaining the temperature between 45-50° C. Following addition of BrCH$_2$CN, the solution was refluxed for 30 min., before allowing the solution to cool down to room temperature. The solvent was removed in vacuo and the residual oil was purified by flash chromatography using CH$_2$Cl$_2$:CH$_3$OH (9:1) as eluent. The title compound was obtained as a straw-coloured oil (3.04 g, 83%). $\delta_h$ (250 MHz; CDCl$_3$); 1.9-2.15 (m, 3H, CH$_2$CH$_2$CH$_2$, 1×CH$_2$CH$_2$CHOH), 2.25 (m, 1H, 1×CH$_2$CH$_2$CHOH), 2.55 (d, OH), 2.85-3 (m, 3H, NCH$_2$CH$_2$, 1×NCH$_2$CH), 3.1 (2×d, 1H, 1×NCH$_2$CH), 3.9 (s, 2H, NCH$_2$CN) and 4.3 (m, 1H, CH$_2$CHOH); FAB MS, m/z (M+H)$^+$141.

Reference Example 2

3-Hydroxymethyl-piperidin-1-yl-acetonitrile (S2)

The method follows that of S1 using 3-piperidinemethanol (4.79 g, 41.59 mmol), BrCH$_2$CN (1.99 g, 16.64 mmol) and dry THF (25 mL). The title-compound was yielded as a straw-coloured oil (2.35 g, 92%) after flash chromatography using CH$_2$Cl$_2$/CH$_3$OH (9:1) as eluent. d$_H$ (250 MHz; CDCl$_3$); 1.05 (m, 1H, CHCH$_2$OH), 1.5-1.9 (m, 5H, OH, CH$_2$CH$_2$CH$_2$ and CH$_2$CH$_2$CH), 2.15 (t, 1H, J=10 Hz, 1×NCH$_2$CH), 2.35 (3×d, 1H, J=4 Hz and J=10 Hz, 1×NCH$_2$CH$_2$), 2.7 (m, 1H, 1×NCH$_2$CH$_2$), 2.85 (2×d, 1H, J=4 Hz and J=12 Hz, 1×NCH$_2$CH), 3.52 (s, 2H, NCH$_2$CN) and 3.45-3.65 (m, 2H, CHCH$_2$OH); d$_C$ (62.9 MHz; CDCl$_3$); 24.43, 26.14, 38.55, 46.75, 52.83, 55.73, 65.88 and 114.74 (CN); FAB MS, m/z (M+H)$^+$ 155.

Reference Example 3

4-Hydroxy-piperidin-1-yl-acetonitrile (S3)

BrCH$_2$CN (28.55 g, 0.238 mmol) was added dropwise to a solution of 4-hydroxypiperidine (24.98 g, 0.216 mol) and Et$_3$N (33.18 mL, 0.238 mmol) in dry THF (100 mL) under N$_2$, maintaining the temperature between 45-50° C. After addition of BrCH$_2$CN, the solution was refluxed for 30 min., before allowing the solution to cool down to room temperature. The title-compound was afforded as a straw-coloured oil (18.97 g, 63%) after purification by flash chromatography using ether/CH$_3$OH (19:1) as eluent. d$_H$ (250 MHz; CDCl$_3$); 1.65 (m, 2H, 1×CH$_2$CH$_2$CH and 1×CHCH$_2$CH$_2$), 1.75 (s, 1H, OH), 1.95 (m, 2H, 1×CH$_2$CH$_2$CH, 1×CHCH$_2$CH$_2$), 2.45 (m, 2H, 1×NCH$_2$CH$_2$ and 1×NCH$_2$CH$_2$), 2.78 (m, 2H, 1×NCH$_2$CH$_2$ and 1×NCH$_2$CH$_2$), 3.55 (s, 2H, NCH$_2$CN) and 3.75 (m, 1H, CH$_2$CHOH); δ$_C$ (62.9 MHz; CDCl$_3$); 33.96, 46.09, 49.73, 66.58 and 114.71 (CN); IR υ$_{max}$/cm$^{-1}$; 3375 (broad), 2230, 1420, 1330, 1150 and 1060; FAB MS, m/z(M+H)$^+$ 141.

Reference Example 4

2-Hydroxymethyl-piperidin-1-yl-acetonitrile (S4)

The method follows that of S3 using 2-piperidinemethanol (26.50 g, 0.230 mol), BrCH$_2$CN (30.35 g, 0.253 mol), Et$_3$N (35.27 mL, 0.253 mol) and dry THF (150 mL). The crude product was purified by flash chromatography using ether/CH$_3$OH (19:1) as eluent. The title-compound was crystallised from ether yielding cream-coloured crystals (31.46 g, 89%). δ$_H$(250 MHz; CDCl$_3$); 1.2-1.85 (m, 6H, NCH$_2$CH$_2$CH$_2$, CH$_2$CH$_2$CH$_2$CH and CH$_2$CH$_2$CH), 2.05 (s (broad), 6H, OH), 2.4 (m, 1H, NCH$_2$CH$_2$), 2.55 (3×d, 1H. 1×NCH$_2$CH$_2$), 2.95 (m, 1H, NCHCH$_2$), 3.45 (d, 1H, J=17 Hz, 1×NCH$_2$CN), 3.5 (2×d, 1H, J=3 Hz and 12 Hz, 1×CHCH$_2$OH), 3.76 (2×d, 1H, J=3 Hz and 12 Hz, CHCH$_2$OH) and 4.05 (d, 1H, J=17 Hz, 1×NCH$_2$CN); δ$_C$ (62.9 MHz; CDCl$_3$); 23.71, 25.25, 28.69, 43.43, 54.04, 60.73, 64.46 and 115.05 (CN); FAB MS, m/z (M+H)$^+$ 155; IR υ$_{max}$/cm$^{-1}$; 3400 (OH, m broad), 2350 and 2240 (CN) and 1650.

Reference Example 5

2-Hydroxymethyl-pyrrolidin-1-yl-acetonitrile (S11)

The method follows that of S3 using 2-pyrrolidinemethanol (24.27 g, 0.241 mol), BrCH$_2$CN (31.81 g, 0.265 mol), Et$_3$N (37 mL, 0.265 mol) and dry THF (150 mL). The product was obtained as a straw-coloured oil (21.60 g, 64%) after purification by flash chromatography using ether/CH$_3$OH (19:1). δ$_H$(250 MHz; CDCl$_3$); 1.5-2.0 (m, 5H, CH$_2$CH$_2$CH$_2$, CH$_2$CH$_2$CH, OH), 2.7 (m, 1H), 2.85 (m, 1H), 3.05 (m, 1H), 3.45 (2×d, 1H, J=4 Hz and J=11 Hz, 1×CHCH$_2$OH), 3.65 (2×d, 1H, J=4 Hz and 11 Hz, 1×CHCH$_2$OH) and 3.75 (d, 2H, NCH$_2$CN); δ$_C$(62.9 MHz; CDCl$_3$); 23.37, 27.45, 40.96, 53.95, 62.43, 63.06 and 115.48(CN); IR υ$_{max}$/cm$^{-1}$; 3375 (NH$_2$), 3300 (NH$_2$), 3200 (OH), 2970-2800 (CH$_2$, CH$_3$), 1600, 1475, 1375, 1230 and 1060; FAB MS, m/z(M+H)$^+$ 141.

Reference Example 6

3-Hydroxy-pyrrolidin-1-yl-acetonitrile (S12)

The method follows that of S3 using 3-hydroxypyrrolidine (15 g, 0.172 mol), BrCH$_2$CN (22.67 g, 0.189 mmol) and dry THF (60 mL). The title-compound was yielded as a straw-coloured oil (15.39 g, 71%) after flash chromatography using CH$_2$Cl$_2$/CH$_3$OH (9:1) as eluent. δ$_H$ (250 MHz; CDCl$_3$); 1.9-2.25 (m, 2H, 2×ring-H), 2.3 (m, 1H, ring-H), 2.65 (d, OH), 2.85-3.05 (m, 3H, 3×ring-H), 3.95 (d, 2H, NCH$_2$CN) and 4.2 (m, 1H, CH$_2$CHOH); FAB MS, m/z (M+H)$^+$ 127.

Reference Example 7

2,6-Bis-hydroxymethyl-piperidin-1-yl-acetonitrile (S5)

Step 1. 2,6-Piperidinedimethanol (S15)
2,6-Pyridinedimethanol (15 g, 107.9 mmol) was suspended in glacial acetic acid (250 mL) and hydrogenated at atmospheric pressure and RT for 48 h using PtO$_2$ (1.5 g) as catalyst. The catalyst was then removed by filtration through celite and the acidic solution was concentrated in vacuo to give an oily residue. The oil was diluted with EtOAc (50 mL) and stirred at ice-cold temperature. A saturated solution of brine and concentrated ammonia (pH~12) was added slowly until the pH was 11-12. The organic phase was then separated from the aqueous phase, which was extracted with EtOAc (3×50 mL). The combined organic phases were dried (MgSO$_4$) followed by filtration and evaporation of solvent under vacuum yielding a straw-coloured oil (5.21 g, 33%). FAB MS, m/z(M+H)$^+$ 146.

Step 2. The method follows that of S5. 2,6-piperidinedimethanol (3.80 g, 26.21 mmol), iodoacetonitrile (5.24 g, 31.45 mmol), Et$_3$N (4.38 mL, 31.45 mmol) and dry DMF (20 mL). Purification by flash chromatography using CH$_2$Cl$_2$/CH$_3$OH (9:1) as eluent afforded the title compound as a straw-coloured oil (2.5 g, 53%). FAB MS, m/z(M+H)$^+$ 185.

The iodoacetonitrile was prepared by the use of the Finkelstein reaction. BrCH$_2$CN (3.77 g, 0.0314 mmol) was added dropwise to a stirred solution of NaI (4.71 g, 0.031 mmol) in acetone. Precipitation of NaBr occurred within a few minutes and indicated that exchange of the halides had taken place. Sodium bromide was filtered off, and the acetone was removed in vacuo. Crude yield (5.24 g, 100%).

Synthesis of Hydroxylated N-2-Aminoethyl Piperidines and Pyrrolidines

Reference Example 8

1-(2-Amino-ethyl)-piperidin-3-ol (S6)

LiAlH$_4$ (2.44 g, 64.2 mmol) was added to dry THF (20 mL) at 0° C. in a three-neck round bottom flask under N$_2$. The solution was stirred for 15 min. before the 3-hydroxypiperidin-1-yl-acetonitrile (3 g, 21.4 mmol), diluted in dry THF (5 mL), was added slowly via syringe. The reaction mixture was then refluxed 5 h before allowing the solution to cool to RT. Excess of LiAlH$_4$ was destroyed by dropwise addition of 2.4 mL of H$_2$O, 2.4 mL of NaOH (15%) and finally EtOAc was added dropwise until no effervesence was observed. The formed granular precipitate (lithium hydroxide and aluminium hydroxide) was filtered off and washed several times with CH$_2$Cl$_2$ and EtOAc. The organic layer was dried (MgSO$_4$) and the solvent was removed in vacuo to yield a thick yellowish oil. The title-compound was purified by kugelrohr distillation (172° C., 0.05 mbar) and obtained as a straw coloured oil (1.95 g, 63%). δ$_H$ (250 MHz; CDCl$_3$); 1.45-1.7 (m, 3H, CH$_2$CH$_2$CH$_2$, 1×CH$_2$CH$_2$CHOH), 1.76 (m, 1H, 1×CH$_2$CH$_2$CHOH), 1.95 (s, 3H, OH, NH$_2$), 2.25-2.55 (m, 6H, H$_2$NCH$_2$CH$_2$, NCH$_2$CH$_2$, NCH$_2$CH), 2.75 (t, 2H, H$_2$NCH$_2$CH$_2$), and 3.9 (m, 1H, CH$_2$CHOH); δ$_C$(62.9 MHz; CDCl$_3$); 21.93, 32.01, 38.88, 53.84, 60.80, 61.06 and 66.36; FAB MS, m/z(M+H)$^+$ 145.

Reference Example 9

[1-(2-Amino-ethyl)-3-piperidin-2-yl-]methanol (S7)

The method follows that of S6 using 3-hydroxymethyl-piperidin-1-yl-acetonitrile (2.95 g, 19.1 mmol), LiAlH$_4$ (2.18 g, 57.3 mmol) and dry THF (15 mL). The title compound (2.30 g, 76%) was afforded as a colourless oil by kugelrohr distillation at (164° C., 0.01 mbar). δ$_H$ (250 MHz; CDCl$_3$);

1.1 (m, 1H, (CHCH$_2$OH), 1.5-1.9 (m, 7H, OH, NH$_2$, CH$_2$CH$_2$CH$_2$ and CH$_2$CH$_2$CH), 1.95 (t, 1H, J=10 Hz, 1×NCH$_2$CH), 2.1 (3×d, 1H, J=3 Hz and 10 Hz, 1×NCH$_2$CH$_2$), 2.4 (t, 2H, J=6 Hz, H$_2$NCH$_2$CH$_2$N), 2.6 (m, 1H, 1×NCH$_2$CH$_2$, 2.8 (t, 3H, J=6 Hz, H$_2$NCH$_2$CH$_2$N and 1×NCH$_2$CH), 3.45-3.65 (m, 2H, CHCH$_2$OH); δ$_C$(62.9 MHz; CDCl$_3$); 24.66, 27.50, 38.19, 38.91, 54.54, 57.43, 61.61 and 66.55; IR υ$_{max}$/cm$^{-1}$; 3375 (broad), 1675, 1625, 1450, 1100 and 1050; FAB MS, m/z(M+H)$^+$ 159.

Reference Example 10

1-(2-Amino-ethyl)-piperidin-4-ol (S8)

The method follows that of S6 using 4-hydroxy-piperidin-1-yl-acetonitrile (18.97 g, 0.136 mol), LiAlH$_4$ (15.48 g, 0.408 mol) and dry THF (150 mL). The title compound (8.56 g, 44%) was afforded as a straw-coloured oil after kugelrohr distillation (178° C., 0.05 mbar). δ$_H$(250 MHz; CDCl$_3$); 1.55 (m, 2H, 1×CHCH$_2$CH$_2$ and 1×CH$_2$CH$_2$CH), 1.85 (m, 2H, 1×CHCH$_2$CH$_2$ and 1×CH$_2$CH$_2$CH), 2-2.25 (m, 5H, NCH$_2$CH$_2$, NCH$_2$CH$_2$ and OH), 2.38 (t, 2H, H$_2$NCH$_2$CH$_2$N), 2.72 (t, 4H, H$_2$NCH$_2$CH$_2$N, NH$_2$) and 3.65 (m, 1H, CH$_2$CHOH); δ$_C$(62.9 MHz; CDCl$_3$); 34.56, 38.98, 51.35, 60.84 and 67.64; FAB MS, m/z(M+H)$^+$ 145; IR υ$_{max}$/cm$^{-1}$; 3375 (broad), 1600, 1460, 1370, 1290 and 1070.

Reference Example 11

[1-(2-Amino-ethyl)-piperidin-2-yl-]methanol (S9)

The method follows that of S6 using 2-hydroxymethyl-piperidin-1-yl-acetonitrile (31.96 g, 0.208 mol), LiAlH$_4$ (23.68 g, 0.624 mol) and dry THF (200 mL). The title compound (8.74 g, 27%) was afforded as straw-coloured oil by kugelrohr distillation (225° C., 0.13 mbar). δ$_H$ (250 MHz; CDCl$_3$); 1.2-1.75 (m, 6H, CH$_2$CH$_2$CH$_2$, CH$_2$CH$_2$CH and CH$_2$CH$_2$CH), 2.2 (m, 1H, 1×NCH$_2$CH$_2$) 2.35 (m, 2H, H$_2$NCH$_2$CH$_2$N), 2.58 (s (broad), 3H, OH and NH$_2$), 2.75 (t, 2H, H$_2$NCH$_2$CH$_2$N), 2.85 (3×d, 1H, 1×NCH$_2$CH$_2$), 2.92 (m, 1H, NCHCH$_2$), 3.4 (2×d, 1H, J=4 Hz and 12 Hz, 1×CHCH$_2$OH) and 3.76 (2×d, 1H, J=4 Hz and 12 Hz, 1×CHCH$_2$OH; FAB MS, m/z(M+H)$^+$ 159.

Reference Example 12

[1-(2-Amino-ethyl)-piperidin-bis-2,6-yl-]methanol (S10)

The method follows that of S6 using 2,6-bis-hydroxymethyl-piperidin-1-yl-acetonitrile (2.40 g, 13.04 mmol), LiAlH$_4$ (1.49 g, 39.13 mmol) and dry THF (30 mL). The title-compound was afforded as a straw-coloured oil without purification (1.03 g, 42%). It was found necessary to stir the dry destroyed LiAlH$_4$ complex in dry THF for 10 h at 40° C. in order to optimise the yield of the desired di-hydroxylated diamine. FAB MS, m/z(M+H)$^+$ 189.

Reference Example 13

[1-(2-Amino-ethyl)-pyrrolidin-2-yl-]methanol (S13)

The method follows that of S6 using 2-hydroxymethyl-pyrrolidin-1-yl-acetonitrile (19.5 g, 0.139 mol), LiAlH$_4$ (15.84 g, 0.417 mol) and dry THF (150 mL). The title-compound (12.5 g, 63%) was afforded as straw-coloured oil by kugelrohr distillation (142° C., 0.3 mbar). δ$_H$ (250 MHz; CDCl$_3$); 1.6-1.9 (m, 4H, CH$_2$CH$_2$CH$_2$, CH$_2$CH$_2$CH), 1.98 (s (broad), 3H, NH$_2$, OH), 2.3 (m, 1H), 2.45 (m, 1H), 2.55 (m, 1H), 2.75-2.85 (m, 3H), 3.19 (m, 1H, NCHCH$_2$), 3.4 (2×d, 1H, J=3 Hz and J=11 Hz, 1×CHCH$_2$OH), 3.6 (2×d, 1H, J=3 Hz and J=11 Hz, 1×CHCH$_2$OH); IR υ$_{max}$/cm$^{-1}$; 3375 (NH$_2$), 3300 (NH$_2$), 3200 (OH), 2970-2800 (CH$_2$, CH$_3$), 1600, 1475, 1375, 1230 and 1060; FAB MS, m/z(M+H)$^+$ 145.

Reference Example 14

1-Amino-ethyl-pyrrolidin-3-ol (S14)

The method follows that of S6 using 3-hydroxy-pyrrolidin-1-yl-acetonitrile (15 g, 0.107 mol), LiAlH$_4$ (10.17 g, 0.268 mol) and dry THF (150 mL). The title compound (9.55 g, 69%) was afforded as a straw-coloured oil and used for the next step without further purification. δ$_H$ (250 MHz; CDCl$_3$); 1.55-1.85 (m, 2H, 2×ring-H), 2.05 (s, 3H, OH, NH$_2$), 2.25-2.55 (m, 6H, 4×ring-H and H$_2$NCH$_2$CH$_2$N), 2.9 (t, 2H, H$_2$NCH$_2$CH$_2$N) and 4.05 (m, 1H, CH$_2$CHOH); FAB MS, m/z(M+H)$^+$ 131.

Preparation of Chromophores

Reference Example 15

1,5-Diamino-4,8-Dihydroxyanthraquinone

In a 2 liter round bottom flask was placed 1,5-diaminoanthracene-9,10-dione (12 g, 50 mmol). Concentrated sulphuric acid (180 g) was added and the mixture was stirred 15 minutes at 0° C. before adding sodium chlorate (14.4 g, 134 mmol) portionwise over 45 minutes. The reaction mixture was allowed to warm up to room temperature where it was left stirred for 3 h before it was poured into 1% solution of chilled sodium hydrogen sulfite (1 L). The precipitated solid was removed by filtration and was washed successively with cold water and then hot water. After lyophilisation overnight, the product (11.3 g, 83%) was obtained as a crude purple-blue solid. FAB MS, m/z(M+H)$^+$ 271.

Reference Example 16

5,8-Dihydroxyleucoquinizarin
(Leuco-1,4,5,8,-tetrahydroxyanthraquinone) (B).

To crude 1,5-diamino-4,8-dihydroxyanthraquinone (11 g, 0.041 mol) was added NaOH (2.5 M, 200 mL) and the suspension was refluxed gently for 3 hours before it was allowed to cool down to room temperature. Sodium hydrogen sulphite (31.74 g, 0.182 mol) was added portionwise and the reaction mixture was refluxed again for 3 hours. It was cooled down to room temperature and was acidified with concentrated hydrochloric acid until pH 3. The precipitate was isolated by filtration and washed successively with cold water and then hot water. After lyophilisation overnight, the title compound was afforded as a crude brown solid (8 g, 73%). FAB MS, m/z (M+H)$^+$ 251.

Reference Example 17

1,4-Difluoro-5,8-Dihydroxyanthraquinone (C)

A mixture of ground AlCl$_3$ (2.955 g, 22.16 mmol), NaCl (432 mg, 7.39 mmol), 1,4-dihydroxybenzene (224 mg, 2.03 mmol) and 3,6-difluorophthalic dry (340 mg, 1.85 mmol) were stirred vigorously in a round bottom flask and heated to 220° C. in an oil-bath for 3 h. The oil-bath was removed and the reaction quenched by addition of ice and concentrated hydrochloric acid (10 mL). The final aqueous solution was filtered under suction and the precipitated material was washed with water followed by freeze-drying. No further work-up was required, as the brown title-compound (470 mg, 92%) was pure as observed by TLC and confirmed by NMR and MS: $\delta_H$(250 MHz; CDCl$_3$); 7.3 (s, 2H), 7.55 (m, 2H), 12.9 (s, 2H); FAB MS, m/z(M+H)$^+$ 277.

Reference Example 18

1-[[2-(Dimethylamino)ethyl]amino]-4-fluoro-5,8-dihydroxyanthracene-9,10-dione (HAQ107)

1,4-Difluoro-5,8-dihydroxyanthraquinone (0.50 g, 1.812 mmol) N,N-dimethylethylenediamine (0.16 g, 1.812 mmol) and pyridine (3 mL) were stirred for 24 h at RT. The mixture was quenched in cold brine (50 mL) and left for 3 hours before the crude product was isolated by filtration. The crude product was chromatographed using a gradient elution from 1 to 5% MeOH in CH$_2$Cl$_2$. The product HAQ107 was afforded as a purple powder (0.24 g, 38%). $\delta_H$(250 MHz; DMSO); 2.35 (s, 6H, 2×NCH$_3$) 2.7 (t, 2H, HNCH$_2$CH$_2$N), 3.5 (q, 2H, HNCH$_2$CH$_2$N), 7.1 (s, 1H), 7.1 (s, 1H), 7.4 (s, 2H, C(6)H and C(7)H), 10.75 (t, 2H, C(1)NH and C(4)NH) and 13.4 (s, 2H, C(5)OH and C(8)OH); $\delta_C$ (62.9 MHz; DMSO); FAB MS, m/z(M+H)$^+$ 344.

Chromophore Substitution Reactions

Examples 1 and 2

Amination of Leucoquinizarin and 5,8-Dihydroxy-leucoquinizarin 1-{[(2-Dimethylamino)ethyl]amino}-4-{[2-(3-hydroxypiperidin-1-yl)ethyl]amino}-anthracene-9,10-dione (HAQ22) and 1,4-Bis-{[2-(3-hydroxypiperidin-1-yl)ethyl]-amino}-anthracene-9,10-dione (HAQ24)

N-N-dimethylethylenediamine (0.92 g, 10.42 mmol) and 1-(2-aminoethyl)-3-piperidin-3-ol (1.50 g, 10.42 mmol) in EtOH (5 mL) were simultaneously added to a suspension of leucoquinizarin (0.63 g, 2.61 mmol) in EtOH (25 mL) under N$_2$. After 8 h of stirring at reflux temperature, the reaction mixture was stirred at RT another 14 h. The EtOH was removed in vacuo and the remaining residue was added to ice-cold brine. The precipitated solid was isolated by filtration and lyophilised. The dark blue solid was flash chromatographed in a short column by first using CH$_2$Cl$_2$ to remove non-polar side-products, then by increasing the polarity gradually removing more side-products and finally by using CH$_2$Cl$_2$/CH$_3$OH (4:1), obtaining the desired crude components. The crude solid was flash chromatographed using CH$_2$Cl$_2$/CH$_3$OH/NH$_3$ (94:6:0.75) as eluent. To obtain pure components a final purification was made by preparative TLC using CH$_2$Cl$_2$/CH$_3$OH/NH$_3$ (94:6:0.75) as eluent. HAQ22 and HAQ24 were afforded as dark-blue solids (0.12 g, 10%) and (0.16 g, 12%) respectively.

HAQ22 $\delta_H$(250 MHz; CDCl$_3$); 1.5 (m, 2H, CH$_2$CH$_2$CH$_2$), 1.8 (m, 1H, 1×CH$_2$CH$_2$CH), 2.0 (m, 1H, 1×CH$_2$CH$_2$CH), 2.2 (t, 1H, 1×NCH$_2$CH$_2$), 2.3 (s, 6H, 2×NCH$_3$), 2.5 (d, 1H, 1×NCH$_2$), 2.6-2.8 (m, 7H, 2×NCH$_2$CH$_2$N, 1×NCH$_2$CH and OH), 3.4 (m, 4H, 2×H$_2$NCH$_2$CH$_2$N), 3.9 (m, 1H, CH$_2$CHOH), 7.1 (d, 2H, C(2)H, C(3)H), 7.62 (m, 2H, C(6)H, C(7)H), 8.32 (m, 2H, C(5)H, C)8)H), 10.75 (t, 2H, C(1)NH) and 11 (t, 1H, C(4)NH); $\delta_C$(62.9 MHz; CDCl$_3$); 21.18, 31.47, 39.72, 41.13, 45.72, 53.06, 56.05, 58.63, 60.06, 65.99, 110.15, 123.55, 126.16, 131.97, 134.48, 145.78 and 182.41; FAB MS, m/z(M+H)$^+$ 437; IR $\upsilon_{max}$/cm$^{-1}$; 3450 (broad, OH), 3220 (NH), 3020 (Ar—CH), 2960-2800 (CH$_2$—CH$_3$), 1650, 1625, 1575, 1480, 1380 and 1220.

HAQ24 $\delta_H$(250 MHz; CDCl$_3$); 1.5-1.9 (m, 10H, 8×ring-H and 2×OH), 2.1 (m, 2H, 2×ring-H), 2.25 (m, 2H, 2×ring-H), 2.5 (d, 2H, 2×ring-H), 2.75-2.95 (m, 6H, 4×ring-H and 2×HNCH$_2$CH$_2$N), 3.5 (q, 4H, 2×HNCH$_2$CH$_2$N), 3.95 (m, 2H, 2×CH$_2$CHOH), 7.2 (s, 2H, C(2)H and C(3)H), 7.65 (m, 2H, C(6)H and C(7)H), 8.35 (m, 2H, C(5)H and C)8)H), and 11.0 (t, 2H, C(1)NH and C(4)NH); FAB MS, m/z (M+H)$^+$ 493.

Figure 2:
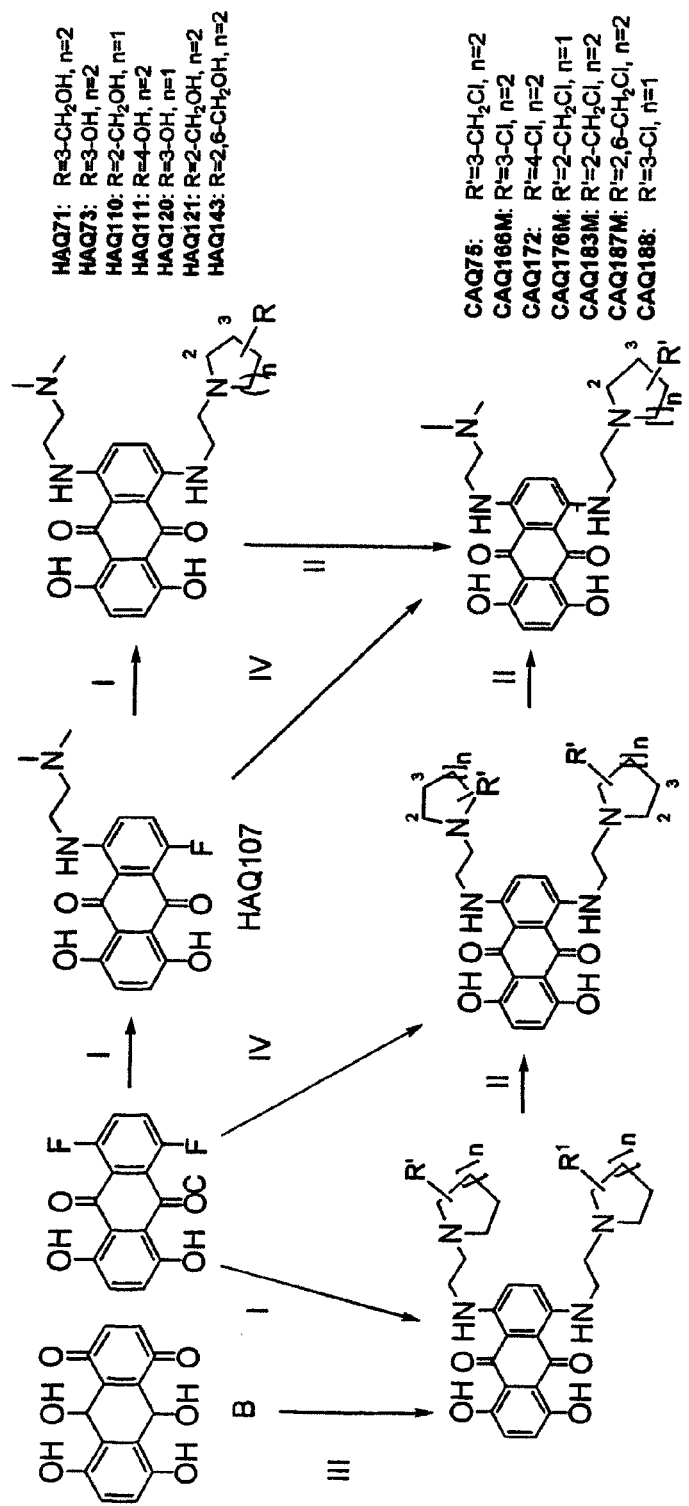
FIG. 2 is a reaction scheme referred to herein as Scheme 3.

The following are examples of the invention and comparative examples. The reaction schemes are shown in schemes 2 (FIG. 1) and 3 (FIG. 2). In these schemes, step (I) is the addition of one amino alkyl amino side chain carried out in pyridine at 90° C. for 30min-1 hr; step (II) is chlorination carried out using (Ph)$_3$PCCl$_y$ and CH$_2$Cl$_2$ and at reflux for 3-1 Oh using ethereal HCl. In scheme 3, step (III) is a further side chain linking step carried out at reflux in ethanol; and step IV is chlorination of the side chain hydroxyl groups carried out in pyridine at 30-60° C. for 2 to 5 h, using ethereal HCl.

Example 3

1,4-Bis-{[2-(3-hydroxymethylpiperidine-1-yl)ethyl]amino}-5,8-dihydroxyanthracene-9,10-dione (HAQ70)

[1-(2-aminoethyl)-piperidin-3-yl]methanol (1.9 g, 12 mmol) in EtOH (2 mL) was added to a stirred suspension of 5,8-dihydroxyleucoquinizarin (272 mg, 1 mmol) in EtOH (15 mL) under N$_2$. After 7 h of stirring at reflux temperature, the reaction mixture was cooled down to RT and stirred for another 16 h. The EtOH was removed in vacuo and the remaining residue was added to ice-cold brine. The precipitated solid was isolated by filtration and lyophilised. The dark blue solid was flash chromatographed using CH$_2$Cl$_2$ followed by gradual increase in polarity to CH$_2$Cl$_2$/CH$_3$OH (4:1). Subsequently, the crude product was flash chromatographed using CH$_2$Cl$_2$/CH$_3$OH/NH$_3$ (94:6:0.75) as eluent. The title compound was afforded as dark-blue solid (115.9 mg, 21%). M.p. 180-183° C.; $\delta_H$ (250 MHz; CDCl$_3$); 1.1-1.95 (m, 12H, 2×OH and 10×ring-H), 2.25 (m, 4H, 4×ring-H ), 2.7 (t, 6H, 2×HNCH$_2$CH$_2$N and 2×ring-H), 2.95 (2×d, 2H, 2×ring-H), 3.5 (m, 4H, 2×HNCH$_2$CH$_2$), 3.65 (m, 4H, 2×CHCH$_2$OH), 7.1 (s, 2H, C(2)H and C(3)H), 7.2 (s, 2H, C(6)H and C(7)H), 10.5 (t, 2H, C(1)NH and C(4)NH) and 13.6 (s, 2H, C(5)OH and C(8)OH); $\delta_C$ (62.9 MHz; CDCl$_3$); FAB MS, m/z(M+H)$^{30}$ 553; IR $\upsilon_{max}$/cm$^{-1}$; 3400 (OH), 3225 (NH), 3100 (Ar—CH), 2960-2800 (CH$_2$, CH$_3$), 1650, 1625, 1575, 1480, 1370 and 1225; Anal. calcd for C$_{30}$H$_{40}$N$_4$O$_6$: C, 65.20; H, 5.47; N, 10.14. Found: C, 65.16; H, 5.49; N, 9.93.

Example 4

1,4-Bis-{[2-(3-hydroxymethylpiperidine-1-yl)ethyl]amino}-anthracene-9,10-dione (HAQ38)

Although not shown in scheme 3, the method follows that of HAQ70 using leucoquinizarin (0.23 g, 0.95 mmol), [1-(2-aminoethyl)-piperidin-3-yl-]methanol (0.06 g, 3.8 mmol) and ethanol (25 mL). The title compound was yielded as a dark-blue solid (0.15 g, 29%). M.p. 112-114° C.; $\delta_H$(250 MHz; CDCl$_3$); 1.15 (m, 2H, 2×CH$_2$CHCH$_2$OH), 1.5-1.75 (m, 6H, 2×CH$_2$CH$_2$CH and 2×CH$_2$CH$_2$CH$_2$), 1.85 (m, 2H, 2×CH$_2$CH$_2$CH), 2.3 (m, 4H, 4×ring-H), 2.5 (s (broad), 4H, 2×ring-H, 2×OH), 2.65 (t, 4H, J=5 Hz, 2×HNCH$_2$CH$_2$N), 2.75 (2×d, 2H, J=3 Hz and 12 Hz, 2×ring-H), 3.42 (q, 4H, J=5 Hz, 2×HNCH$_2$CH$_2$N), 3.55 (2×d, 2H, J=5 Hz and 12 Hz, 2×CHCH$_2$OH), 3.7 (2×d, 2H, J=9 Hz and 12 Hz, 2×CHCH$_2$OH), 7.1 (s, 2H, C(2)H and C(3)H), 7.6 (m, 2H, C(6)H and C(7)H), 8.3 (m, 2H, C(5)H, C(8)H) and 10.75 (t, 2H, C(1)NH and C(4)NH); $\delta_C$(62.9 MHz; CDCl$_3$); 24.08, 26.92, 37.90, 40.52, 54.43, 56.95, 57.75, 65.70, 109.89, 123.87, 126.13, 132.09, 134.46, 146.6 and 182.36; FAB MS, m/z(M+H)$^+$ 521; IR $\upsilon_{max}$/cm$^{-1}$; 3400 (OH), 3090 (Ar—CH), 2960-2800 (CH$_2$, CH$_3$), 1650, 1585, 1550, 1520, 1265, 1175 and 1125; Anal. calcd for C$_{30}$H$_{40}$N$_4$O$_4$: C, 69.21; H, 7.74; N, 10.76. Found: C, 69.22; H, 7.88; N, 10.69.

Ipso Substitution of Fluorides of 1,4-Difluoro-5,8-dihydroxyanthraquinone by Diamine Example 5

1-[(2-Dimethylamino)ethylamino]-4-[2-(3-hydroxymethyl-piperidin-1-yl)ethylamino]-5,8-dihydroxy-anthracene-9,10-dione (HAQ71)

The method follows that of HAQ105 (see Example 7 below) using HAQ107 (200 mg, 0.581 mmol), [1-(2-aminoethyl)-piperidin-3-yl-]methanol (350 mg, 2.215 mmol), pyridine (2 mL), 90° C., 30 min. The product was afforded as a dark blue powder (190 mg, 68%). M.p. 181-183 ° C.; $\delta_H$(250 MHz; CDCl$_3$); 1.2 (m, 2H, 2×ring-H), 1.6-1.9 (m, 5H, OH and 4×ring-H), 2.18-2.3 (m, 2H, ring-H), 2.35 (s, 6H, 2×NCH$_3$), 2.6-2.75 (m, 4H, 2×HNCH$_2$CH$_2$N), 2.9 (2×d, 1H, 1×ring-H), 3.46 (m, 4H, 2×HNCH$_2$CH$_2$N), 3.65 (2×d, 2H, CHCH$_2$OH), 7.15 (s, 2H, C(2)H and C(3)H), 7.2 (s, 2H, C(6)H and C(7)H), 10.4 (t, 1H, C(1)H), 10.5 (t, 1H, C(4)H), 13.5 (s, 1H, C(8)H) and 13.6 (s, 1H, C(5)H); $\delta_C$ (62.9 MHz; CDCl$_3$); 24.33, 26.92, 38.29, 40.03, 40.87, 45.42, 54.23, 57.03, 58.20, 65.99, 108.97, 115.33, 123.43, 123.65, 124.51, 145.99, 146.09, 155.32, and 184.98; FAB MS, m/z(M+H)$^+$ 483; IR $\upsilon_{max}$/cm$^{-1}$; 3425 (OH), 3225 (NH), 3100 (Ar—CH), 2975-2800 (CH$_2$, CH$_3$), 1650, 1625, 1575, 1490, 1360 and 1225; Anal. calcd for C$_{26}$H$_{34}$N$_4$O$_5$: C, 64.71; H, 7.10; N, 11.61. Found: C, 64.81; H, 7.14; N, 11.56.

Example 6

1-[(2-Dimethylamino)ethylamino]-4-[2-(3-hydroxypiperidon-1-yl)ethylamino]-5,8-dihydroxy-anthracene-9,10-dione (HAQ73)

The method follows that of HAQ105 using HAQ107 (120 mg, 0.349 mmol), 1-(2-aminoethyl)-piperidin-3-ol (150 mg, 1.047 mmol), pyridine (1 mL), 30 min, 90° C. The product was afforded as a dark blue powder (95 mg, 58%). M.p. 228-230° C.; $\delta_H$ (250 MHz; CDCl$_3$); 1.55-1.75 (m, 4H, 4×ring-H), 1.83-2.0 (m, 2H, 2×ring-H), 2.28 (2×d, 1H, ring-H), 2.35 (s, 6H, 2×NCH$_3$), 2.65-2.75 (2×t, 5H, 2×HNCH$_2$CH$_2$N and OH), 3.46 (m, 4H, HNCH$_2$CH$_2$N), 3.9 (m, 1H, NCH$_2$CHOH), 7.1 (s, 2H, C(2)H and C(3)H), 7.15 (s, 2H, C(6)H and C(7)H), 10.4 (t, 1H, C(1)H), 10.6 (t, 1H, C(4)H), 13.4 (s, 1H, C(8)H) and 13.5 (s, 1H, C(5)H); $\delta_C$(62.9 MHz; DMSO); 21.48, 31.52, 39.99, 41.26, 45.61, 53.31, 56.14, 58.43, 60.20, 66.03, 109.11, 115.43, 115.48, 123.81, 124.70, 146.29, 155.51, and 185.24; FAB MS, m/z(M+H)$^+$ 469; IR $\upsilon_{max}$/cm$^{-1}$; 3425 (OH), 3240 (NH), 3100 (Ar—CH), 2975-2800 (CH$_2$, CH$_3$), 1650, 1625, 1575, 1490, 1375 and 1225; Anal. calcd for C$_{28}$H$_{36}$N$_4$O$_6$: C, 64.09; H, 6.88; N, 11.96. Found: C, 63.88; H, 6.89; N, 11.98.

Example 7

1,4-Bis-{[2-(2-hydroxymethylpiperidine-1-yl)ethyl]amino}-5,8-dihydroxy-anthracene-9,10-dione (HAQ105)

1,4-Difluoro-5,8-hydroxyanthraquinone (0.17 g, 0.601 mmol) and [1-(2-aminoethyl)-piperidin-2-yl-]methanol (0.95 g, 6.01 mmol) were stirred in pyridine (2 mL) at 90° C. for 1 h. The reaction mixture was added to ice-cold brine and set aside at 4° C. overnight. The precipitated solid was isolated by filtration and lyophilised. The desired product was purified by flash chromatography, initially eluting with CH$_2$Cl$_2$/CH$_3$OH (95:5) to remove non-polar impurities, followed by a gradual increase of CH$_3$OH to CH$_2$Cl$_2$/CH$_3$OH (85:15). The chromatographed product was then crystallised from CHCl$_3$ affording the title compound HAQ105 as a dark blue powder (0.11 g, 34%). M.p. 208-210° C.; $\delta_H$ (250 MHz; DMSO); 1.15-1.65 (m, 12H, 2×OH and 10×ring-H), 2.25-2.4 (m, 6H, 6×ring-H), 2.6-2.7 (t, 4H, 2×HNCH$_2$CH$_2$N), 2.85 (m, 2H, 2×ring-H), 3.55 (t, 4H, 2×HNCH$_2$CH$_2$N), 3.6-3.65 (2×d, 4H, 2×CHCH$_2$OH), 7.2 (s, 2H, C(2)H and C(3)H), 7.5 (s, 2H, C(6)H and C(7)H), 10.75 (t, 2H, C(1)NH and C(4)NH) and 13.65 (s, 2H, C(5)OH and C(8)OH); $\delta_C$ (62.9 MHz; DMSO); 22.55, 24.92, 28.14, 50.99, 52.32, 61.94, 62.42, 107.03, 116.11, 123.89, 125.91, 147.07, 154.46, and 182.88; FAB MS, m/z(M+H)$^+$ 553; IR $\upsilon_{max}$/cm$^{-1}$; 3400 (OH), 3225 (NH), 3100 (Ar—CH), 2960-2800 (CH$_2$, CH$_3$), 1650, 1625, 1575, 1480, 1370 and 1225; Anal. calcd for C$_{30}$H$_{40}$N$_4$O$_6$.1H$_2$O: C, 63.14; H, 7.24; N, 9.82. Found: C, 63.07; H, 7.49; N, 9.77.

Example 8

1-{[(2-Dimethylamino)ethyl]amino}-4-{[2-(2-hydroxymethylpyrrolidin-1-yl)ethyl]-amino}-5,8-dihydroxy-anthracene-9,10-dione (HAQ110)

The method follows that of HAQ105 using HAQ107 (75 mg, 0.218 mmol), [1-(2-aminoethyl)-pyrrolidin-2-yl-]methanol (650 mg, 4.114 mmol), pyridine (2 mL), 1 h, 90° C. The product HAQ110 was afforded as a dark blue powder (52 mg, 51%). M.p. 202-203° C.; $\delta_H$ (250 MHz; DMSO/CDCl$_3$ (1:1)); 1.55-1.9 (m, 4H, 4×ring-H), 2.3 (s, 6H, 2×NCH$_3$), 2.5-2.55 (m, 1H, 1×ring-H), 3.25-3.4 (m, 7H, 2×HNCH$_2$CH$_2$N, 2×ring-H and OH), 3.45-3.6 (m, 6H, 2×HNCH$_2$CH$_2$N and NCHCH$_2$OH), 7.05 (s, 2H, C(2)H and C(3)H), 7.2 (m, 2H, C(6)H and C(7)H), 10.6-10.7 (2×t, 2H, C(1)NH and C(4)NH), and 13.5 (s, 2H, C(5)OH, C(8)OH); $\delta_C$(62.9 MHz; DMSO/CDCl$_3$(1:1)); 22.71, 27.65, 41.58, 44.83, 53.38, 53.53, 57.54, 64.07, 64.94, 107.10, 114.81, 123.73, 125.00, 125.11, 146.52, 154.36, and 183.17; FAB MS, m/z(M+H)$^+$ 469; Anal. calcd for C$_{25}$H$_{32}$N$_4$O$_5$: C, 64.09; H, 6.88; N, 11.96. Found: C, 63.83; H, 6.99; N, 12.05.

Example 9

1-{[(2-Dimethylamino)ethyl]amino}-4-{[2-(4-hydroxypiperidin-1-yl)ethyl]amino}-5,8-dihydroxy-anthracene-9,10-dione (HAQ111)

The method follows that of HAQ105 using HAQ107 (18 mg, 0.0523 mmol), N-(2-aminoethyl)-piperidin-4-ol (140 mg, 0.97 mmol), pyridine (1 mL), 1 h, 90° C. The product HAQ111 was afforded as a dark blue powder (16.1 mg, 65%).

M.p. 231-233° C.; $\delta_H$(250 MHz; DMSO/CDCl$_3$(1:1)); 1.25-1.8 (m, 6H, 6×ring-H), 2.2-2.25 (m, 2H, 2×ring-H), 2.35 (s, 6H, 2×NCH$_3$), 2.5-2.8 (m, 5H, 2×HNCH$_2$CH$_2$N and 1×OH), 3.5-3.55 (m, 5H, 2×HNCH$_2$CH$_2$N and NCH$_2$CHOH), 7.1 (s, 2H, C(2)H and. C(3)H), 7.25 (m, 2H, C(6)H and C(7)H), 10.65 (t, 2H, C(1)NH and C(4)NH), and 13.65 (s, 2H, C(5)OH, C(8)OH); $\delta_C$(62.9 MHz; DMSO/CDCl$_3$(1:1)); 27.78, 32.15, 43.72, 49.49, 54.73, 56.39, 65.09, 106.48, 113.66, 122.55, 123.12, 123.39, 144.97, 153.33, 182.56; FAB MS, m/z(M+H)$^+$ 469; Anal. calcd for C$_{25}$H$_{32}$N$_4$O$_5$. 1 H$_2$O: C, 61.17; H, 6.84; N, 11.52. Found: C, 61.27; H, 6.64; N, 11.40.

Example 10

1,4-Bis-{[2-(3-hydroxypyrrolidin-1-yl)ethyl]amino}-5,8-dihydroxy-anthracene-9,10-dione (HAQ115)

Although not shown in scheme 3 the method follows that of HAQ105 using 1,4-difluoro-5,8-hydroxy-anthraquinone (75 mg, 0.272 mmol), 1-(2-aminoethyl)-pyrrolidin-3-ol (1 g, 7.7 mmol), pyridine (2 mL), 1 h, 100° C. The product HAQ115 was afforded as a dark blue powder (59.2 mg, 44%). M.p. 197-199° C.; $\delta_H$(250 MHz; DMSO/CDCl$_3$(1:1)); 1.55-1.65 (m, 2H, 2×ring-H), 2.0-2.1 (m, 2H, 2×ring-H), 2.45-2.9 (m, 10H, 8×ring-H and 2×OH), 2.75-2.85 (t, 4H, 2×HNCH$_2$CH$_2$N), 3.55-3.65 (q, 4H, 2×HNCH$_2$CH$_2$N), 4.05-4.15 (m, 2H, 2×CH$_2$CHOH), 7.05 (s, 2H, C(2)H and C(3)H), 7.3 (m, 2H, C(6)H and C(7)H), 10.55 (t, 2H, C(1)NH and C(4)NH), and 13.55 (s, 2H, C(5)OH, C(8)OH); $\delta_C$ (62.9 MHz; DMSO/CDCl$_3$(1:1)); 28.01, 34.73, 41.22, 52.18, 54.42, 62.33, 69.26, 107.01, 115.04, 123.79, 124.90, 146.43, 154.38, and 183.21; FAB MS, m/z(M+H)$^+$ 497; Anal. Calcd for C$_{26}$H$_{32}$N$_4$O$_6$: C, 62.88; H, 6.51; N, 11.28. Found: C, 62.50; H, 6.54; N, 11.00.

Example 11

1,4-Bis-{[2-(4-hydroxypiperidin-1-yl)ethyl]amino}-5,8-dihydroxy-anthracene-9,10-dione (HAQ116)

The method follows that of HAQ105 using 1,4-difluoro-5,8-hydroxy-anthraquinone (45 mg, 0.163 mmol), 1-(2-aminoethyl)-piperidin-4-ol (1 g, 42.6 mmol), pyridine (2 mL), 1 h, 90° C. The product HAQ116 was afforded as a dark blue powder (36.2 mg, 42%). M.p. 241-244° C.; $\delta_H$(250 MHz; CDCl$_3$); 1.25-1.65 (m, 12H, 12×ring-H), 1.7-2.0 (m, 4H, 4×ring-H), 2.65-3.0 (m, 6H, 2×NCH$_2$CH$_2$N and 2×OH), 3.6-3.8 (q, 4H, 2×HNCH$_2$CH$_2$N), 4.1 (m, 2H, 2×CH$_2$CHOH), 7.2 (s, 2H, C(2)H and C(3)H), 7.6 (m, 2H, C(6)H and C(7)H), 10.5 (t, 2H, C(1)NH and C(4)NH), and 13.6 (s, 2H, C(5)OH, C(8)OH); $\delta_C$(62.9 MHz; CDCl$_3$); 31.67, 39.45, 41.56, 49.56, 54.66, 109.22, 115.40, 124.82, 125.45, 146.39, 154.70, 164.022, and 183.54; FAB MS, m/z(M+H)$^+$ 525.

Example 12

1-{[(2-Dimethylamino)ethyl]amino}-4-([2-(3-hydroxypyrrolidin-1-yl)ethyl]amino)-5,8-dihydroxy-anthracene-9,10-dione (HAQ120)

The method follows that of HAQ105 using HAQ107 (45 mg, 0.13 mmol), 1-(2-aminoethyl)-pyrrolidin-3-ol (880 mg, 6.77 mmol), pyridine (1 mL), 30 min, 100° C. The product HAQ120 was afforded as a dark blue powder (24 mg, 41%). M.p. 195-198° C.; $\delta_H$(250 MHz; DMSO/CDCl$_3$(1:1)); 1.55-1.7 (m, 1H, 1×ring-H), 1.95-2.05 (m, 2H, 2×ring-H), 2.3 (s, 6H, 2×NCH$_3$), 2.35-2.4 (m, 1H, 1×ring-H), 2.5-2.6 (t, 4H, 2×HNCH2CH$_2$N), 2.6-2.85 (m, 2H, 1×ring-H and OH), 3.5-3.55 (q, 4H, 2×HNCH$_2$CH$_2$N), 4.25 (m, 1H, CH$_2$CHOH), 7.1 (s, 2H, C(2)H and C(3)H), 7.4 (m, 2H, C(6)H and C(7)H), 10.5 (t, 2H, C(1)NH and C(4)NH), and 13.5 (s, 2H, C(5)OH, C(8)OH); $\delta_C$(62.9 MHz; DMSO/CDCl$_3$(1:1)); 34.19, 41.22, 52.18, 54.42, 62.33, 69.26, 107.18, 114.78, 123.79, 124.90, 146.90, 154.38, and 183.16; FAB MS, m/z(M+H)$^+$ 455.

Example 13

1-{[(2-Dimethylamino)ethyl]amino}-4-{[2-(2-hydroxymethylpiperidin-1-yl)ethyl]-amino}-5,8-dihydroxy-anthracene-9,10-dione (HAQ121)

The method follows that of HAQ105 using HAQ107 (30 mg, 0.0872 mmol), [1-(2-aminoethyl)-piperidin-2-yl-]methanol (700 mg, 4.43 mmol), pyridine (1 mL), 30 min, 100° C. The product HAQ121 was afforded as a dark blue powder (21.3 mg, 51%). M.p. 201-203° C.; $\delta_H$(250 MHz; CDCl$_3$); 1.7-2.1 (m, 7H, 6×ring-H and OH), 2.6 (s, 6H, 2×NCH$_3$), 2.8 (m, 2H, 2×ring-H), 2.9 (t, 4H, 2×HNCH$_2$CH$_2$N), 2.9-3.1 (m, 1H, 1×NCHCH$_2$), 3.6-3.65 (t, 4H, 2×HNCH$_2$CH$_2$N) 3.9-4.1 (2×, 2H, CHCH$_2$OH), 7.05 (s, 2H, C(2)H and C(3)H), 7.15 (m, 2H, C(6)H and C(7)H), 10.5 (t, 2H, C(1)NH and C(4)NH), and 13.65 (s, 2H, C(5)OH, C(8)OH); $\delta_C$(62.9 MHz; CDCl$_3$); 23.06, 23.93, 26.94, 40.57, 41.13, 45.59, 50.42, 51.88, 58.35, 61.44, 62.65, 108.67, 115.43, 123.45, 124.12, 146.11, 155.24, and 184.63; FAB MS, m/z(M+H)$^+$ 483; Anal. calcd for C$_{26}$H$_{34}$N$_4$O$_5$: C, 64.71; H, 7.10; N, 11.61. Found: C, 64.45; H, 6.85; N, 11.79.

Example 14

1,4-Bis-{[2-(2-hydroxymethylpyrrolidin-1-yl )ethyl]amino}-5,8-dihydroxy-anthracene-9,10-dione (HAQ125)

As shown in scheme 3 the method follows that of HAQ105 using 1,4-difluoro-5,8-hydroxy-anthraquinone (75 mg, 0.272 mmol), [1-(2-aminoethyl)-pyrrolidin-2-yl-]methanol (1.5 g, 10.42 mmol) pyridine (2 mL), 2 h, 100° C. The product HAQ125 was afforded as a dark blue powder (58.1 mg, 41%). M.p. 202-204° C.; $\delta_H$(250 MHz; DMSO/CDCl$_3$(1:1)); 1.6-1.9 (m, 8H, 8×ring-H), 2.2-2.3 (m, 2H, 2×ring-H), 2.6-2.75 (m, 6H, 2×HNCH$_2$CH$_2$N and 2×ring-H), 3.1-3.2 (m, 2H, 2×ring-H), 3.3-3.6 (m, 10H, 2×HNCH$_2$CH$_2$N, 2×NCHCH$_2$OH and 2×OH), 7.1 (s, 2H, C(2)H and C(3)H), 7.5 (m, 2H, C(6)H and C(7)H), 10.7 (t, 2H, C(1)NH and C(4)NH), and 13.55 (s, 2H, C(5)OH, C(8)OH); $\delta_C$(62.9 MHz; DMSO/CDCl$_3$(1:1)); 22.75, 27.65, 41.59, 53.56, 64.08, 64.96, 107.14, 114.92, 123.79, 125.30, 146.65, 154.37, and 183.15; FAB MS, m/z(M+H)$^+$ 525; Anal. calcd for C$_{28}$H$_{36}$N$_4$O$_6$: C, 64.14; H, 6.87; N, 10.69. Found: C, 64.09; H, 6.98; N, 10.77.

Example 15

1-{[2-(2,6-Dihydroxymethylpiperidine-1-yl)ethyl]-amino}-4-{[(2-Dimethylamino)ethyl]amino}-5,8-dihydroxyanthracene-9,10-dione (HAQ143)

The method follows that of HAQ105 using HAQ107 (78 mg, 0.227 mmol), [1-(2-aminoethyl)-piperidin-bis-2,6-yl-]methanol (420 mg, 2.283 mmol), pyridine (2 mL), 30 min, 100° C. The product HAQ143 was afforded as a dark blue powder (63 mg, 54%). M.p. 216-218° C.; $\delta_H$(250 MHz; CDCl$_3$); 1.4-1.8 (m, 6H, 6×ring-H), 2.35 (s, 6H, 2×NCH$_3$), 2.65 (t, 2H, 1×HNCH$_2$CH$_2$N), 2.75-2.85 (s, 2H, 2×NCHCH$_2$), 3.0 (t, 2H, HNCH$_2$CH$_2$N), 3.35-3.45 (m, 6H, 2×HNCH$_2$CH$_2$N and 2×OH), 3.7 (d, 4H, 2×CHCH$_2$OH) 7.05 (s, 2H, C(2)H and C(3)H), 7.15 (m, 2H, C(6)H and C(7)H), 10.5 (t, 2H, C(1)NH and C(4)NH), and 13.65 (s, 2H, C(5)OH, C(8)OH); δ$_C$(62.9 MHz; CDCl$_3$); 20.90, 24.85, 41.27, 42.35, 45.63, 50.50, 58.42, 61.95, 64.60, 107.01, 115.38, 123.89, 124.92, 146.39, 155.85, and 185.21; FAB MS, m/z(M+H)$^+$ 513; Anal. calcd for C$_{27}$H$_{36}$N$_4$O$_6$: C, 63.26; H, 7.08; N, 10.93. Found: C, 62.93; H, 7.12; N, 10.84.

Example 16

1-{[2-(2-Hydroxymethylpyrrolidin-1-yl)ethyl]amino}-anthracene-9,10-dione (HAQ163)
(scheme 2)

To [1-(2-aminoethyl)-pyrrolidin-2-yl-]methanol (1.63 g, 11.3 mmol) in pyridine (10 mL) was added 1-chloroanthraquinone (1.37 g, 5.646 mmol), and the mixture was stirred at 65° C. for 24 hours. Pyridine was removed in vacuo and the resulting mixture of oil and solid was dissolved in CH$_2$Cl$_2$ and washed with H$_2$O (3×50 mL) to remove any unreacted amine. The separated organic layer was removed in vacuo and the crude product was chromatographed using CH$_2$Cl$_2$/CH$_3$OH (97:3). The desired product was yielded as a red powder (0.21 g, 11%). M.p. 113-115° C.; δ$_H$(250 MHz; CDCl$_3$); 1.75-2.0 (m, 4H), 2.25-2.35 (m, 1H), 2.6-2.8 (m, 2H), 3.15-3.3 (m, 2H), 3.35-3.55 (m, 4H), 3.75-3.85 (2×d, 1H), 7.0 (2×d, 1H), 7.45-7.6 (m, 2H), 7.65-7.8 (m, 2H), 8.2 (2×d, H), 8.45 (2×d), and 10.05 (s, 1H, C(1)NH); δ$_C$(62.9 MHz; CDCl$_3$); 24.11, 27.15, 41.64, 52.99, 53.82, 62.61, 65.26, 113.15, 115.60, 126.57, 132.86, 133.81, 135.32, 151.49, 183.77, and 184.89; FAB MS, m/z(M+H)$^+$ 351; Anal. calcd for C$_{21}$H$_{22}$N$_2$O$_3$: C, 71.98; H, 6.33; N, 8.00. Found: C, 71.79; H, 6.13; N, 8.07.

Example 17

1-{[2-(3-Chloropiperidin-1-yl)ethyl]amino}-4-{[(2-dimethylamino)ethyl]amino}-5,8-dihydroxyanthracene-9,10-dione (CAQ166M)

Figure 4:
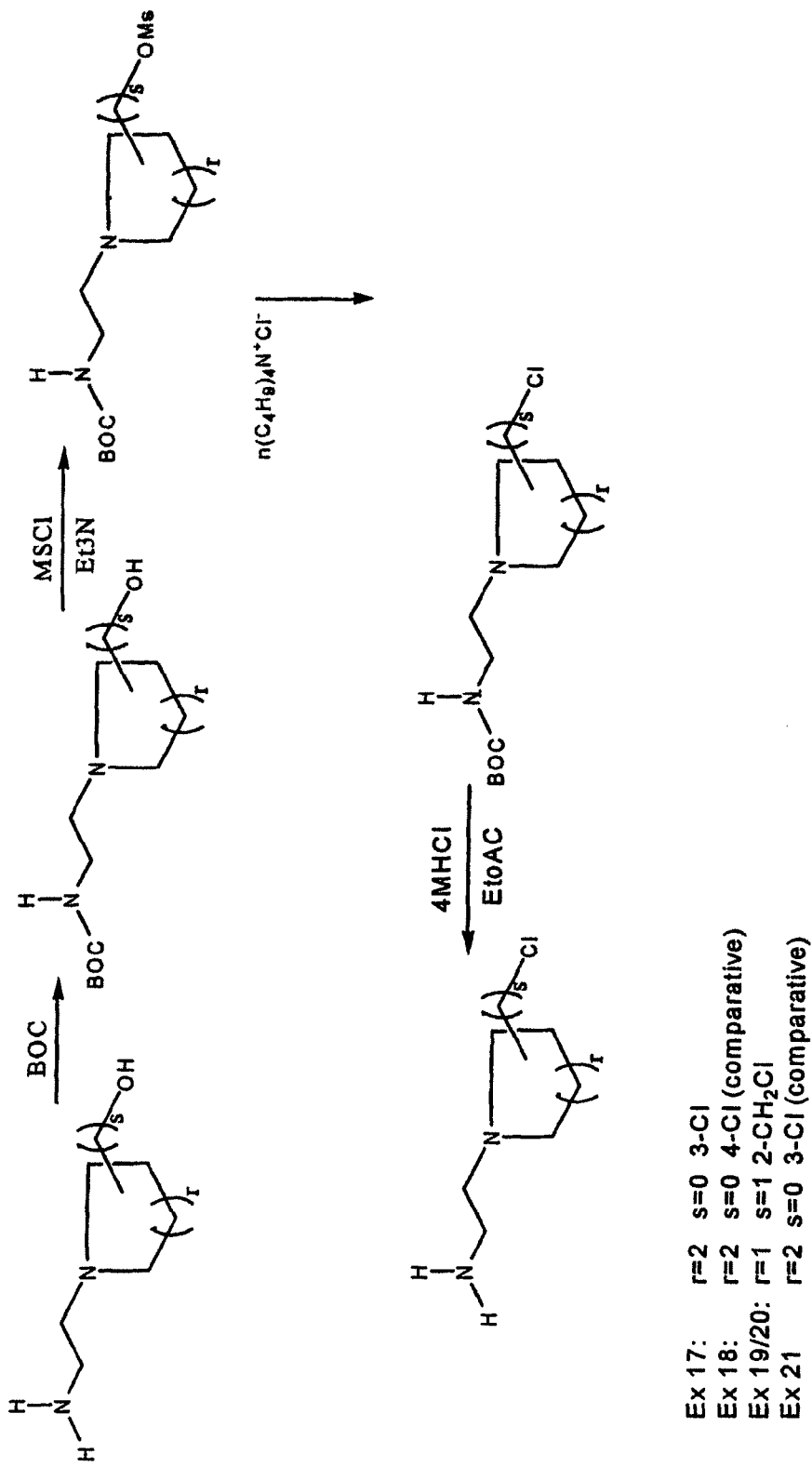
FIG. 4 is a reaction scheme referred to herein as Scheme 5.
The following examples illustrate the invention.

Preparation of CAQ166M involved 5 steps, where none of the intermediate products were isolated and purified. The preparation generally follows scheme 5 (FIG. 4) then scheme 3 (FIG. 2).
(i): Boc protection of mono-hydroxylated diamine sidechains
(ii): Mesylation of Boc-protected mono-hydroxylated diamine sidechains
(iii): Chlorination of mono-mesylated diamine sidechains
(iv): Deprotection of Boc group of chlorinated diamine sidechain
(v): Ipso substitution of fluoride of 1-[[2-(dimethylamino)ethyl]amino]-4-fluoro-5,8-dihydroxyanthraquinone by chlorinated diamine (i) 1-(2-Aminoethyl)-piperidin-3-ol (1 g, 6.94 mmol) and Et$_3$N (1.16 mL, 8.33 mmol) was stirred together with CH$_3$OH (10 mL) for 5 min. before Boc$_2$O (1.82 g, 8.33 mmol), dissolved in CH$_3$OH (5 mL), was added dropwise over 15-20 min. The reaction mixture was then stirred 20 h at 45° C., before being concentrated in vacuo. The oil was diluted in EtOAc (40 mL) and washed with 2×H$_2$O (20 mL) and brine (20 mL). The organic phase was dried with magnesium sulphate (MgSO$_4$), and after filtration was concentrated in vacuo yielding a straw-coloured oil that needed no further purification (1.35 g, 80%).

FAB MS, m/z(M+H)$^+$ 245.

(ii) MsCl (420 μL, 5.41 mmol) was added dropwise to an ice-cold solution of the Boc-protected amine (880 mg, 3.61 mmol) and Et$_3$N (755 μL, 5.41 mmol) in dry CH$_2$Cl$_2$ (10 mL) under N$_2$. After the reaction mixture was stirred for 1 h at 0° C., the solution was diluted with cold CH$_2$Cl$_2$, washed with ice-cold NaHCO$_3$ and ice-cold brine. The organic phase was dried with MgSO$_4$, filtered and concentrated in vacuo at room temperature. The mesylated product was afforded as a crude straw-coloured oil (965 mg, 83%). FAB MS, m/z(M+H)$^+$ 323.

(iii) Tetra-n-butylammonium chloride (2 g, 7.20 mmol) was added to a stirred solution of the crude mesylate (965 mg, 3.01 mmol) in dry DMF (5 mL). The reaction mixture was heated at 90° C. for 30 min. before DMF was removed in vacuo. The residual oil was taken up in CH$_2$Cl$_2$ and washed with ice-cold NaHCO$_3$ and ice-cold brine. The organic phase was dried (MgSO$_4$), filtered and solvent was concentrated in vacuo at room temperature. The crude product was yielded as a straw-yellowish-coloured oil (624 mg, 79%). FAB MS, m/z(M+H)$^+$ 263.

(iv) The crude chloride (624 mg, 2.38 mmol) was stirred in 4 M HCl in EtOAc for an hour to remove the Boc group. To the acidic EtOAc solution, cooled in an ice-bath, was slowly added a solution of brine and NH$_3$ (pH=12) until the aqueous phase was pH~11. The chlorinated diamine was then extracted into the organic phase, which was dried with (MgSO$_4$). The solvent was removed in vacuo and the crude product was yielded as a brownish oil (175 mg, 45%) that was used directly in the next step. FAB MS, m/z(M+H)$^+$ 163.

(v) A mixture of HAQ107 (36 mg, 0.105 mmol) and the crude Boc-deprotected chloride (175 mg, 1.08 mmol) was reacted in pyridine (2 mL) at RT for 2 h. The reaction mixture was concentrated in vacuo and the crude product was purified by initially eluting with CH$_2$Cl$_2$ to remove non-polar impurities, followed by a gradual increase of CH$_3$OH to CH$_2$Cl$_2$/CH$_3$OH (97:3). The chromatographed product was crystallised from CHCl$_3$. The title compound CAQ166M was yielded as a dark blue solid (35 mg, 60%). M.p. dec.>300° C.; δ$_H$(250 MHz; CDCl$_3$); 1.5-1.9 (m, 4H, 4×ring-H), 2.15-2.25 (m, 3H, 3×ring-H), 2.35 (s, 6H, 2×NCH$_3$), 2.65-2.8 (2×t, 4H, 2×HNCH$_2$CH$_2$N), 3.15-3.2 (2×d, 1H, ring-H), 3.45 (t, 4H, 2×HNCH$_2$CH$_2$N), 4.1 (m, 1H, CH$_2$CHCl), 7.05 (s, 2H, C(2)H and C(3)H), 7.15 (s, 2H, C(6)H and C(7)H), 10.45 (t, 2H, C(1)NH and C(4)NH), and 13.5 (s, 2H, C(5)OH, C(8)OH); δ$_C$(62.9 MHz; CDCl$_3$); 24.95, 29.65, 34.88, 40.37, 41.26, 45.63, 52.85, 55.78, 56.28, 58.39, 61.43, 109.23, 115.39, 123.64, 123.78, 124.66, 146.05, 146.24, 155.41, 185.28, and 185.35; FAB MS, m/z(M+H)$^+$ 487.

Example 18

1-{[2-(4-Chloropiperidin-1-yl)ethyl]amino}-4-{[(2-dimethylamino)ethyl]amino}-5,8-dihydroxyanthracene-9,10-dione (CAQ172)

The method follows that of CAQ166M.
(i) 1-(2-Aminoethyl)-piperidin-4-ol (2 g, 13.89 mmol) Et$_3$N (2.32 mL, 16.65 mmol), CH$_3$OH (20 mL), Boc$_2$O (3.63 g, 16.65 mmol), dissolved in CH$_3$OH (5 mL). The reaction mixture was stirred 18 h. The product was afforded as a strawcoloured oil that needed no further purification (2.35 g, 69%). FAB MS, m/z(M+H)$^+$ 245.

(ii) Boc-protected amine (1.70 g, 6.94 mmol), MsCl (810 μL, 10.41 mmol), Et$_3$N (1.45 mL, 10.41 mmol), dry CH$_2$Cl$_2$ (20 mL). The mesylated product was afforded as a crude straw-coloured oil (1.39 g, 62%). FAB MS, m/z(M+H)$^+$ 323.

(iii) Crude mesylate (1.39 g, 4.29 mmol), tetra-n-butylammonium chloride (2.38 g, 8.58 mmol), dry DMF (10 mL), 120° C., 30 min. The crude chloride was afforded as a straw/yellowish-coloured oil (0.73 g, 65%). FAB MS, m/z(M+H)$^+$ 263.

(iv) Crude chloride (0.73 g, 2.78 mmol), 4M HCl EtOAc, 1 h. The crude Boc-deprotected amine was afforded as a brownish oil (160 mg, 35%). FAB MS, m/z(M+H)$^+$ 163.

(v) HAQ107 (36 mg, 0.105 mmol), crude deprotected sidechain (160 mg, 0.98 mmol) pyridine (2 mL), 5 h, 45° C. The title compound (CAQ172) was afforded as a dark blue solid (31.4 mg, 54%). M.p. 200-202° C.; $\delta_H$(250 MHz; CDCl$_3$); 1.3-1.75 (m, 6H, 6×ring-H), 1.95-2.1 (m, 2H, 2×ring-H), 2.35 (s, 6H, 2×NCH$_3$), 2.6-2.8 (t, 4H, 2×HNCH$_2$CH$_2$N), 3.3 (q, 4H, 2×HNCH$_2$CH$_2$N), 3.45 (m, 1H, CH$_2$CHCl), 7.05 (s, 2H, C(2)H and C(3)H), 7.1 (s, 2H, C(6)H and C(7)H), 10.45 (t, 2H, C(1)NH and C(4)NH), and 13.55 (s, 2H, C(5)OH, C(8)OH); $\delta_C$(62.9 MHz; CDCl$_3$); 24.06, 34.69, 45.38, 50.79, 56.25, 58.96, 109.09, 115.31, 123.77, 123.95, 124.61, 146.12, 146.22, 155.34, 161.33, and 185.29; FAB MS, m/z(M+H)$^+$ 487; Anal. calcd for C$_{25}$H$_{31}$ClN$_4$O$_4$.2HCl.3H$_2$O: C, 48.90; H, 6.24; N, 9.12. Found: C, 48.77; H, 6.00; N, 9.10.

Example 19

1-{[2-(2-Chloromethylpyrrolidin-1-yl)ethyl]-amino}-4-{[(2-Dimethylamino)ethyl]amino}-5,8-dihydroxyanthracene-9,10-dione (CAQ176M)

The method follows that of CAQ166M.

(i) [1-(2-Aminoethyl)-pyrrolidin-2-yl-]methanol (5 g, 34.72 mmol) Et$_3$N (5.8 mL, 41.67 mmol), CH$_3$OH (40 mL), Boc$_2$O (9.10 g, 41.67 mmol), dissolved in CH$_3$OH (10 mL). The reaction mixture was stirred 18 h. The product was afforded as a strawcoloured oil that needed no further purification (6.9 g, 82%).

(ii) Boc-protected amine (5.1 g, 20.9 mmol), MsCl (2.43 mL, 31.35 mmol), Et$_3$N (4.32 mL, 31.35 mmol), dry CH$_2$Cl$_2$ (50 mL). The mesylated product was afforded as a crude straw-coloured oil (5.63 g, 84%). FAB MS, m/z(M+H)$^+$ 245.

(iii) Crude mesylate (5.63 g, 17.48 mmol), tetra-n-butylammonium chloride (9.72 g, 11.26 mmol), dry DMF (30 mL), 90° C., 30 min. The crude chloride was afforded as a straw/yellowish-coloured oil (2.2 g, 48%). FAB MS, m/z(M+H)$^+$ 323.

(iv) Crude chloride (2 g, 7.58 mmol), 4M HCl EtOAc, 1 h. The crude Boc-deprotected amine was afforded as a brownish oil (675 mg, 55%). FAB MS, m/z(M+H)$^+$ 263.

(v) HAQ107 (95 mg, 0.276 mmol), crude deprotected sidechain (675 mg, 4.15 mmol), pyridine (2 mL), 2 h, 30° C. The title compound CAQ176M was afforded as a dark blue solid (63.8 mg, 41%). FAB MS, m/z(M+H)$^+$ 163. M.p. 253-255° C.; $\delta_H$(250 MHz; CDCl$_3$); 1.5-1.85 (m, 4H, 4×ring-H), 2-2.25 (m, 3H, 3×ring-H), 2.35 (s, 6H, 2×NCH$_3$), 2.6-2.8 (2×t, 4H, 2×HNCH$_2$CH$_2$N), 3.15 (d, 1H, 1×NCHCH$_2$Cl), 3.4 (m, 5H, 2×HNCH$_2$CH$_2$N and 1×NCHCH$_2$Cl), 7.05 (s, 2H, C(2)H and C(3)H), 7.1 (s, 2H, C(6)H and C(7)H), 10.45 (t, 2H, C(1)NH and C(4)NH), and 13.55 (s, 2H, C(5)OH, C(8) OH); $\delta_C$(62.9 MHz; CDCl$_3$); 24.93, 34.86, 40.33, 41.19, 45.59, 52.82, 55.78, 56.03, 56.27, 58.35, 61.43, 109.02, 115.40, 123.55, 123.69, 124.49, 146.01, 146.2, 155.32, and 185.11; FAB MS, m/z(M+H)$^+$ 487; Anal. calcd for C$_{25}$H$_{31}$ClN$_4$O$_4$.2HCl.2H$_2$O: C, 50.38; H, 6.60; N, 9.40. Found: C, 49.81; H, 6.23; N, 9.29.

Example 20

1,4-Bis-{[2-(2-chloromethylpyrrolidin-1-yl)ethyl]amino}-5,8-dihydroxyanthracene-9,10-dione (CAQ177M)

The method follows that of CAQ166M.

(i) [1-(2-Aminoethyl)-pyrrolidin-2-yl-]methanol (7 g, 48.61 mmol) Et$_3$N (8.12 mL, 58.33 mmol), CH$_3$OH (50 mL), Boc$_2$O (12.73 g, 58.33 mmol), dissolved in CH$_3$OH (15 mL). The reaction mixture was stirred 20 h. The product was afforded as a strawcoloured oil that needed no further purification (9.36 g, 79%). FAB MS, m/z(M+H)$^+$ 245.

(ii) Boc-protected amine )8 g, 32.8 mmol), MsCl (3.81 mL, 49.2 mmol), Et$_3$N (6.85 mL, 49.2 mmol), dry CH$_2$Cl$_2$ (50 mL). The product was afforded as a crude straw-coloured oil (9.06 g, 86%). FAB MS, m/z(M+H)$^+$ 323.

(iii) Crude mesylate (9 g, 28 mmol), tetra-n-butylammonium chloride (13.34 g, 42 mmol), dry DMF (50 mL), 90° C., 30 min. The crude product was afforded as a straw-coloured oil (6.78 g, 61%). FAB MS, m/z(M+H)$^+$ 263.

(iv) Crude chloride (6.78 g, 25.7 mmol), 4M HCl EtOAc, 1 h. The crude Boc-deprotected amine was afforded as a brownish oil (1.98 g, 47%). FAB MS, m/z(M+H)$^+$ 163.

(v) HAQ107 (125 mg, 0.363 mmol), crude deprotected sidechain (1.98 mg, 12.1 mmol), pyridine (5 mL), 4 h, 30° C. The title compound CAQ177M was yielded as a dark blue solid (88.5 mg, 39%). M.p. dec.>300° C.; $\delta_H$(250 MHz; DMSO); 1.45-1.85 (m, 6H, 6×ring-H), 2.15-2.35 (m, 6H, 6×ring-H), 2.65-2.85 (m, 6H, 2×HNCH$_2$CH$_2$N and 2×ring-H), 3.15 (d, 2H, 2×NCHCH$_2$Cl), 3.45-3.55 (q, 4H, 2×HNCH$_2$CH$_2$N), 4.15 (m, 2H, 2×NCHCH$_2$Cl) 7.05 (s, 2H, C(2)H and C(3)H), 7.15 (s, 2H, C(6)H and C(7)H), 10.45 (t, 2H, C(1)NH and C(4)NH), and 13.45 (s, 2H, C(5)OH, C(8) OH); $\delta_C$ (62.9 MHz; DMSO), 28.11, 35.05, 41.78, 50.83, 55.43, 60.52, 65.26, 107.91, 114.93, 124.33, 127.56, 144.33, 156.69, 183.28; FAB MS, m/z(M+H)$^+$ 561; Anal. calcd for C$_{28}$H$_{34}$Cl$_2$N$_4$O$_4$.2HCl: C, 53.05; H, 5.72; N, 8.84. Found: C, 53.35; H, 5.84; N, 8.72.

Example 21

1-{[2-(3-Chloropyrrolidin-1-yl)ethyl]amino}-4-{[(2-dimethylamino)ethyl]amino}-5,8-dihydroxyanthracene-9,10-dione (CAQ188M)

The method follows that of CAQ166M.

(i) 1-(2-Aminoethyl)-pyrrolidin-3-ol (1 g, 7.94 mmol) Et$_3$N (1.32 mL, 9.52 mmol), CH$_3$OH (10 mL), Boc$_2$O (2.08 g, 9.52 mmol), dissolved in CH$_3$OH (5 mL). The reaction mixture was stirred 16 h. The product was afforded as a strawcoloured oil that needed no further purification (1.54 g, 86%). FAB MS, m/z(M+H)$^+$ 230.

(ii) Boc-protected amine (960 mg, 4.16 mmol), MsCl (483 μL, 6.24 mmol), Et$_3$N (868 μL, 6.24 mmol), dry CH$_2$Cl$_2$ (10 mL). The crude product was afforded as a straw-coloured oil (1 g, 78%). FAB MS, m/z(M+H)$^+$ 308.

(iii) Crude mesylate (1 g, 3.24 mmol), tetra-n-butylammonium chloride (1.35 g, 4.86 mmol), dry DMF (10 mL), 100° C., 30 min. The product was afforded as a straw-/yellowish coloured oil (705 mg, 81%). FAB MS, m/z(M+H)$^+$ 248.

(iv) Crude chloride (705 mg, 2.88 mmol), 4M HCl EtOAc, 1 h. The crude Boc-deprotected amine was afforded as a brownish oil (124 mg, 30%). FAB MS, m/z(M+H)$^+$ 148.

(v) HAQ107 (50 mg, 0.18 mmol), crude deprotected sidechain (124 mg, 0.86 mmol) pyridine (2 mL), 2 hours, 60° C. The product CAQ188M was afforded as a dark blue powder (15 mg, 15%). M.p. dec.>300° C.; $\delta_H$(250 MHz; DMSO/CDCl$_3$(1:1)); 1.8-2.15 (m, 2H, 2×ring-H), 2.3 (m, 1H, ring-H), 2.35 (s, 6H, 2×NCH$_3$), 2.85-3.05 (m, 7H), 3.8-4.1 (m, 5H), 7.1 (s, 2H, C(2)H and C(3)H), 7.2 (s, 2H, C(6)H and C(7)H), 10.45 (t, 2H, C(1)NH and C(4)NH), and 13.55 (s, 2H, C(5)OH, C(8)OH); $\delta_C$(62.9 MHz; CDCl$_3$); 37.19, 42.31, 52.01, 55.05, 62.05, 68.95, 107.65, 114.40, 124.91, 125.15, 146.09, 154.74, 184.44; FAB MS, m/z(M+H)$^+$ 473; Anal. calcd for C$_{24}$H$_{29}$ClN$_4$O$_4$.2HCl.4H$_2$O: C, 46.65; H, 6.04; N, 9.07. Found: C, 47.10; H, 5.80; N, 9.07.

Chlorination of Hydroxylated Anthraquinone Using Ph$_3$P—CCl$_4$ Complex

Example 22

1,4-Bis-{[2-(3-chloromethylpiperidin-1-yl)ethyl]amino}-anthracene-9,10-dione (CAQ39)

Ph$_3$P (377.7 mg, 1.44 mmol) and CCl$_4$ (425 μL, 432 mmol) were stirred for 15 min. before it was added dropwise to a stirred solution of HAQ38 (125 mg, 0.24 mmol) in dry CH$_2$Cl$_2$ (5 mL) under N$_2$ at reflux temperature. The reaction mixture was kept at reflux temperature for 4 h before it was cooled down to RT. Ethereal HCl was added to the solution and after 1 h of stirring, the precipitated solid was filtered off. To remove excess of Ph$_3$P and Ph$_3$PO, the precipitated solid was dissolved in warm CH$_3$OH (10 mL). While stirring the dark blue solution at reflux, a mixture of EtOAc and EtOH (1:1) was added until precipitation of solid was observed. The solution was set aside for 1 h before the precipitated product was isolated by filtration; the excess Ph$_3$P and Ph$_3$PO remained in the EtOAc/EtOH solution. The title compound was afforded as a dark blue solid (98.3 mg, 65%). M.p. dec.>300° C.; $\delta_H$ (250 MHz; CDCl$_3$); 1.1 (m, 2H, 2×CH$_2$CHCH$_2$Cl), 1.75 (m, 6H, CH$_2$CH$_2$CH and 2×CH$_2$CH$_2$CH$_2$), 2.05 (m, 4H, ring-H), 2.18 (3×d, 2H, J=3 Hz and 10 Hz, 2×NCH$_2$CH$_2$), 2.73 (t, 4H, J=9 Hz, 2×HNCH$_2$CH$_2$N), 2.8 (m, 2H, ring-H), 2.96 (2×d, 2H, 2×NCH$_2$CH), 3.5 (m, 8H, 2×CHCH$_2$Cl and 2×HNCH$_2$CH$_2$N), 7.25 (s, 2H, C(2)H and C(3)H), 7.7 (m, 2H, C(6)H and C(7)H), 8.3 (m, 2H, C(5)H, C(8)H) and 10.75 (t, 2H, C(1)NH and C(4)NH); d$_C$(62.9 MHz; CDCl$_3$); 24.42, 28.34, 38.47, 40.56, 48.14, 54.22, 57.52, 57.60, 110.30, 123.52, 126.12, 132.01, 134.56, 145.82 and 182.65; FAB MS, m/z(M+H)$^+$ 557; IR $\upsilon_{max}$/cm$^{-1}$; 3400 (NH), 3090, 2960-2825 (CH$_2$, CH$_3$), 1650, 1600, 1585, 1525, 1275, 1025 and 740; Anal. calcd for C$_{30}$H$_{38}$Cl$_2$N$_4$O$_2$.2HCl.2H$_2$O: C, 54.06; H, 6.65; N, 8.41. Found: C, 54.07; H, 6.27; N, 8.14.

Example 23

1-{[2-(3-Chloropiperidin-1-yl)ethyl]amino}-4-{[(2-dimethylamino)ethyl]amino}-anthracene-9,10-dione (CAQ46M)

The method follows that of CAQ39 using HAQ22 (167 mg, 0.384 mmol), Ph$_3$P (302 mg, 0.152 mmol), CCl$_4$(333 μL, 3.456 mmol) and dry CH$_2$Cl$_2$ (2 mL). The reaction was stopped after 6 hours of reflux. The title compound was afforded as a dark blue solid (131 mg, 75%). $\delta_H$(250 MHz; CDCl$_3$); 1.4-1.8 (m, 4H, CH$_2$CH$_2$CH$_2$ and CH$_2$CH$_2$CH), 2.2 (3×d, 1H, J=3 Hz and 11 Hz, 1×NCH$_2$CH$_2$), 2.25 (d, 1H, J=11 Hz, 1×NCH$_2$CH), 2.35 (s, 6H, 2×NCH$_3$), 2.7 (t, 2H, J=7 Hz, HNCH$_2$CH$_2$N), 2.75 (t, 2H, J=7 Hz, HNCH$_2$CH$_2$N), 2.9 (m, 1H, 1×NCH$_2$CH$_2$), 3.15 (2×d, 1H, J=3 Hz and 11 Hz, 1×NCH$_2$CH), 3.5 (m, 4H, 2×HNCH$_2$CH$_2$N), 4.05 (m, 1H, CH$_2$CHCl), 7.1 (d, 2H, C(2)H, C(3)H), 7.6 (m, 2H, C(6)H, C(7)H), 8.3 (m, 2H, C(5)H, C(8)H), and 10.75 (t, 2H, C(1)NH and C(4)NH); $\delta_C$(62.9 MHz; CDCl$_3$); 24.50, 34.95, 40.42, 41.02, 45.65, 52.99, 55.88, 56.85, 58.55, 61.61, 110.23, 123.41, 126.12, 132.03, 134.48, 145.73 and 182.62; FAB MS, m/z(M+H)$^+$ 455.

Example 24

1,4-Bis-{[2-(3-chloromethylpiperidin-1-yl)ethyl]amino}-5,8-dihydroxyanthracene-9,10-dione (CAQ74)

The method follows that of CAQ39 using HAQ70 (142 mg, 0.26 mmol), Ph$_3$P (404 mg, 1.54 mmol), CCl$_4$ (447 μL, 4.63 mmol) and 5 mL CHCl$_3$/CH$_3$CN (4:1) as solvent. The reaction was stopped after 5 hours of reflux. The title compound was yielded as a dark blue solid (117 mg, 68%). M.p. dec.>300° C.; $\delta_H$(250 MHz; CDCl$_3$/D$_2$O (10:1)); 1.4 (m, 2H, 2×CH$_2$CHCH$_2$OH), 1.85-2.3 (m, 8H, 8×ring-H), 3.0 (m, 4H, ring-H), 3.4-3.8 (m, 16H, 2×HNCH$_2$CH$_2$N, 2×HNCH$_2$CH$_2$N] and 8×ring-H), 6.96 (s, 2H, C(2)H and C(3)H) and 7 (s, 2H, C(6)H and C(7)H); $\delta_C$ (62.9 MHz; CDCl$_3$/D$_2$O (10:1)), 27.99, 38.45, 40.03, 48.97, 56.36, 58.40, 111.43, 117.38, 126.78, 127.37, 148.32, 156.32, and 187.18; FAB MS, m/z(M+H)$^+$ 589; Anal. calcd for C$_{30}$H$_{38}$Cl$_2$N$_4$O$_4$.2HCl.2H$_2$O: C, 51.59; H, 6.35; N, 8.02. Found: C, 51.49; H, 6.14; N, 8.22.

Example 25

1-{[2-(2-Chloromethylpiperidin-1-yl)ethyl]amino}-4-{[(2-dimethylamino)ethyl]amino}-5,8-dihydroxy-anthracene-9,10-dione (CAQ75)

The method follows that of CAQ39 using HAQ71 (48 mg, 0.1 mmol), Ph$_3$P (78.7 mg, 0.3 mmol), CCl$_4$ (300 μL, 3.11 mmol) and dry CH$_2$Cl$_2$ (10 mL). The reaction was stopped after 5 hours of reflux. The product (CAQ75) was afforded as a dark blue powder (46.3 mg, 81%). M.p. dec.>300° C.; $\delta_H$(250 MHz; DMSO:CDCl$_3$(1:1)); 1.3-1.45 (m, 3H, 3×ring-H), 1.45-1.6 (m, 2H, 2×ring-H), 2.35 (s, 6H, 2×NCH$_3$), 2.9-3 (m, 6H), 3-3.2 (m, 2H), 3.9 (m, 4H), 4.1 (d, 2H, CHCH$_2$Cl), 7.15 (s, 2H, C(2)H and C(3)H), 7.6 (s, 2H, C(6)H and C(7)H), 10.45 (t, 2H, C(1)NH and C(4)NH), and 13.35 (s, 2H, C(5)OH, C(8)OH); $\delta_C$(62.9 MHz; CDCl$_3$); 22.45, 25.33, 41.70, 42.56, 54.63, 54.95, 61.95, 107.94, 114.43, 124.41, 125.03, 145.03, 145.81, 155.05, and 184.03; FAB MS, m/z(M+H)$^+$ 501; Anal. calcd for C$_{26}$H$_{33}$ClN$_4$O$_4$.2HCl.2H$_2$O: C, 51.20; H, 6.44; N, 9.19. Found: C, 51.30; H, 6.18; N, 9.01.

Example 26

1-{[2-(2-Chloromethylpiperidin-1-yl)ethyl]-amino}-4-{[(2-dimethylamino)ethyl]amino}-5,8-dihydroxy-anthracene-9,10-dione (CAQ183M)

The method follows that of CAQ39 using HAQ121 (105 mg, 0.21 mmol), Ph$_3$P (165.23 mg, 0.63 mmol), CCl$_4$ (500 μL, 5.25 mmol) and dry CH$_2$Cl$_2$ (10 mL). The reaction was stopped after 3 hours of reflux. The product (CAQ183M) was afforded as a dark blue powder (88.8 mg, 73%). M.p. 233-235° C.; $\delta_H$(250 MHz; CDCl$_3$); 1.55-2.1 (m, 8H, 8×ring-H), 2.8 (s, 6H, 2×NCH$_3$), 3.2-3.35 (m, 4H), 3.6-3.75 (m, 2H), 3.9-4.15 (m, 4H), 4.2 (m, 1H), 7.15 (s, 2H, C(2)H and C(3)H), 7.6 (s, 2H, C(6)H and C(7)H), 10.45 (t, 2H, C(1)NH and C(4)NH), and 13.35 (s, 2H, C(5)OH, C(8)OH); $\delta_C$(62.9 MHz; CDCl$_3$); 21.60, 26.03, 36.70, 42.21, 51.73, 54.85, 62.25, 108.34, 114.23, 124.81, 124.93, 145.83, 145.90, 154.65, and 184.20; FAB MS, m/z(M+H)$^+$ 501; Anal. calcd for C$_{26}$H$_{33}$ClN$_4$O$_4$.2HCl.3H$_2$O: C, 49.73; H, 6.58; N, 8.92. Found: C, 50.09; H, 6.27; N, 8.96.

Example 27

1-{[2-(2,6-Dichloromethylpiperidin-1-yl)ethyl]-amino}-4-{[(2-dimethylamino)ethyl]amino}-5,8-dihydroxyanthracene-9,10-dione (CAQ187M)

The method follows that of CAQ39 using HAQ143 (14 mg, 0.0273 mmol), Ph$_3$P (43 mg, 0.164 mmol), CCl$_4$ (79 μL, 0.82 mmol) and dry CH$_2$Cl$_2$ (5 mL). The reaction was stopped after 5 hours of reflux. The product (CAQ187M) was afforded as a dark blue powder (12.2 mg, 81%). $\delta_H$(250 MHz; CDCl$_3$); 1.3-1.65 (m, 6H, 6×ring-H), 2.35 (s, 6H, 2×NCH$_3$), 2.7 (t, 2H, 1×HNCH$_2$CH$_2$N), 2.8-2.9 (m, 2H, 2×NCHCH$_2$), 3.0 (t, 2H, 1×HNCH$_2$CH$_2$N), 3.35-3.45 (q, 4H, 2×HNCH$_2$CH$_2$N), 3.8-3.9 (d, 4H, 2×CHCH$_2$Cl) 7.1 (s, 2H, C(2)H and C(3)H), 7.15 (m, 2H, C(6)H and C(7)H), 10.55 (t, 2H, C(1)NH and C(4)NH), and 13.65 (s, 2H, C(5)OH, C(8)OH); FAB MS, m/z(M+H)$^+$ 549.

Example 28

1,4-Bis-{[2-(2-chloromethylpiperidin-1-yl)ethyl]amino}-5,8-dihydroxyanthracene-9,10-dione (CAQ190M)

The method follows that of CAQ39 using HAQ105 (60 mg, 0.109 mmol), Ph$_3$P (171.5 mg, 0.654 mmol), CCl$_4$ (190 μL, 1.96 mmol) and dry CH$_2$Cl$_2$ (5 mL). The reaction was stopped after 5 hours of reflux. The product (CAQ190M) was afforded as a dark blue powder (49.8 mg, 78%). M.p. decompose>300° C.; $\delta_H$(250 MHz; DMSO); 1.5-1.65 (m, 4H, 4×ring-H), 1.75-2.15 (m, 10H, 10×ring-H), 3.4-3.8 (m, 8H, 2×HNCH$_2$CH$_2$N and 4×ring-H), 4-4.1 (q, 4H, 2×HNCH$_2$CH$_2$N), 4.15 (2×d, 4H, 2×NCHCH$_2$Cl) 7.2 (s, 2H, C(2)H and C(3)H), 7.65 (s, 2H, C(6)H and C(7)H), 10.45 (t, 2H, C(1)NH and C(4)NH), and 13.45 (s, 2H, C(5)OH, C(8)OH); $\delta_C$ (62.9 MHz; DMSO), 26.11, 37.05, 42.78, 50.78, 51.83, 60.32, 62.26, 108.41, 114.33, 125.00, 126.56, 145.93, 154.69, 184.28; FAB MS, m/z(M+H)$^{+589}$.

Example 29

1-{[2-(2-chloromethylpyrrolidin-1-yl)ethyl]amino}-anthracene-9,10-dione (CAQ191M)

The method follows that of CAQ39 using HAQ163 (115 mg, 0.329 mmol), Ph3P (260 mg, 0.99 mmol), CCl4 (100 μL, 9.86 mmol) and dry CH2Cl2 (5 mL). The reaction was stopped after 3 hours of reflux. The product (CAQ191M) was afforded as a orange powder (91.9 mg, 69%). M.p. 250-253° C.; δH(250 MHz; CDCl3); 1.6-2.1 (m, 4H), 2.15-2.35 (m, 1H), 2.65-2.75 (m, 2H), 3.05-3.15 (m, 2H), 3.4-3.6 (m, 4H), 3.8 (2×d, 1H), 7.2 (2×d, 1H), 7.45-7.65 (m, 2H), 7.75-7.95 (m, 2H), 8.1-8.3 (m, 2H), and 9.95 (s, 1H, C(1)NH); δC (62.9 MHz; CDCl3); FAB MS, m/z(M+H$^+$ 351; Anal. calcd for C$_{28}$H$_{36}$N$_4$O$_6$: C, 62.23; H, 5.47; N, 6.91. Found: C, 62.15; H, 5.11; N, 6.77.

Figure 3:
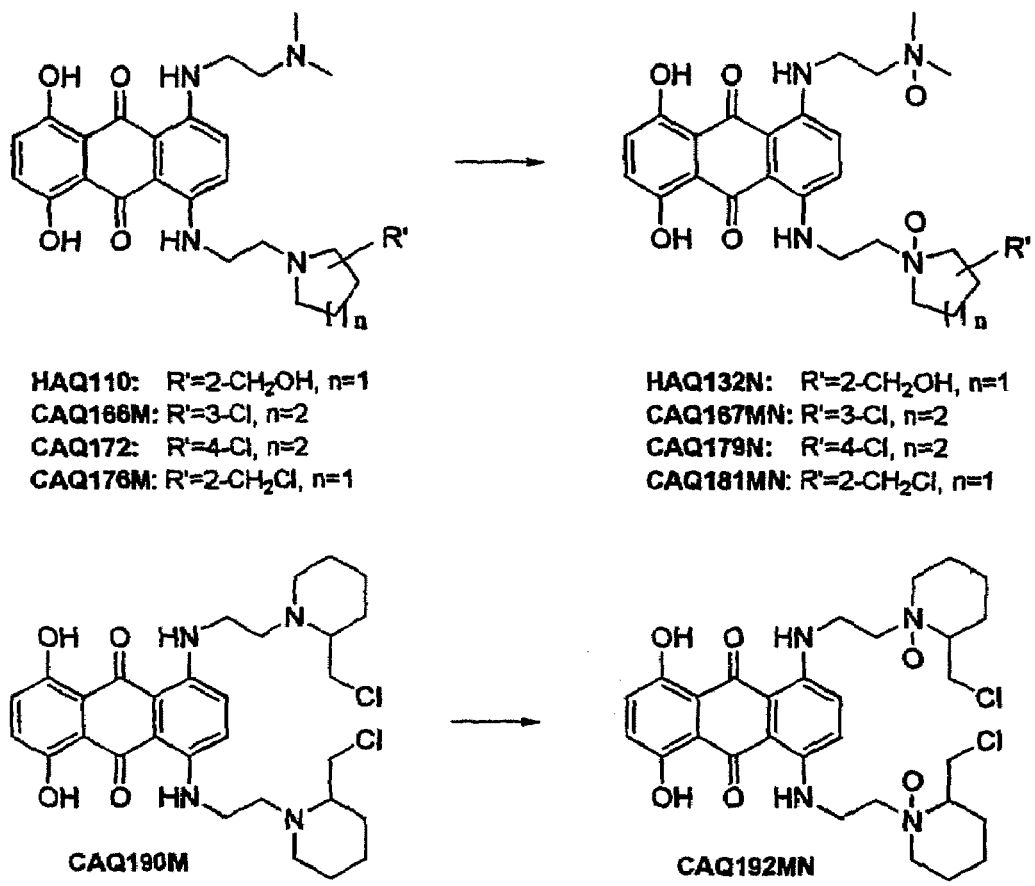
FIG. 3 is a reaction scheme referred to herein as Scheme 4.

N-oxide Derivatisation (Scheme 4, FIG. 3)

Example 30

1-{[2-(2-Hydroxymethylpyrrolidin-1-yl-N-oxide)ethyl]amino}-4-{[(2-dimethylamino-N-oxide)ethyl]amino}-5,8-dihydroxy-anthracene-9,10-dione (HAQ132N)

The oxidising agent m-chloroperoxy benzoic acid acid m-CPBA (25 mg, 0.145 mmol) dissolved in dry dimethyldioxirine DCM (1 mL) was added dropwise to a stirred solution of HAQ110 (20 mg, 0.043 mmol) in dry CH$_2$Cl$_2$ (5 mL) under N$_2$. After 15 minutes of stirring at −10° C. (acetone-ice bath), the reaction was stirred 3 h at 4° C. The solution was then diluted with hexane and after 2 h, the precipitated solid was filtered off and washed successively with ice-cold hexane, ether, CH$_2$Cl$_2$ and EtOAc. The crude product HAQ132N was afforded as a crude dark blue solid (15.5 mg, 73%). Anal. calcd for C$_{25}$H$_{32}$N$_4$O$_7$: C, 59.99; H. 6.44; N, 11.19. Found: C, 52.94; H, 6.15; N, 10.01.

Example 31

1-{[2-(3-Chloropiperidin-1-yl-N-oxide)ethyl]amino}-4-{[(2-dimethylamino-N-oxide)ethyl]amino}-5,8-dihydroxyanthracene-9,10-dione (CAQ167MN)

The method follows that of HAQ132N using CAQ166M (19 mg, 0.0391 mmol), m-CPBA (21.6 mg, 0.125 mmol), dry CH$_2$Cl$_2$ (5 mL). The product CAQ167MN was afforded as a crude dark blue solid (12.5 mg, 62%). Anal. calcd for C$_{25}$H$_{31}$ClN$_4$O$_6$: C, 57.86; H, 6.02; N, 10.8. Found: C, 54.82; H, 4.93; N, 7.43.

Example 32

1-{[2-(4-Chloropiperidin-1-yle-N-oxide)ethyl]amino}-4-{[(2-dimethylamino-N-oxide)ethyl]amino}-5,8-dihydroxyanthracene-9,10-dione (CAQ179N)

The method follows that of HAQ132N using CAQ172 (17 mg, 0.035 mmol), m-CPBA (21.5 mg, 0.119 mmol), dry CH$_2$Cl$_2$ (5 mL). The product CAQ179N was afforded as a crude dark blue solid (15.5 mg, 86%). Anal. calcd for C$_{25}$H$_{31}$ClN$_4$O$_6$: C, 57.86; H, 6.02; N, 10.80. Found. C, 54.62; H, 4.84; N, 6.80.

Example 33

1-{[2-(2-Chloromethylpyrrolidin-1-yl-N-oxide)ethyl]amino}-4-{[(2-dimethylamino-N-oxide)ethyl]amino}-5,8-dihydroxyanthracene-9,10-dione (CAQ181MN)

The method follows that of HAQ132N using CAQ176M (48.3 mg, 0.0994 mmol), m-CPBA (58.3 mg, 0.338 mmol), dry CH$_2$Cl$_2$ (10 mL). The product CAQ181MN was afforded as a crude dark blue solid (46.2 mg, 90%). Anal. calcd for C$_{25}$H$_{31}$ClN$_4$O$_6$: C, 57.86; H, 6.02; N, 10.80. Found: C, 54.66; H, 4.51; N, 6.81.

Example 34

1,4-Bis-{[2-(2-chloromethylpiperidin-1-yl-N-oxide)ethyl]amino}-5,8-dihydroxyanthracene-9,10-dione (CAQ192MN)

The method follows that of HAQ132N using CAQ190M (11 mg, 0.0187 mmol), m-CPBA (12.9 mg, 0.075 mmol), dry $CH_2Cl_2$ (5 mL). The product CAQ192MN was afforded as a crude dark blue solid (10.2 mg, 83%). Anal. calcd for $C_{30}H_{38}Cl_2N_4O_6$: C, 57.97; H, 6.16; N, 9.01. Found: C, 55.46; H, 4.49; N, 6.93.

Comparative Example 1

1,4-Bis-{[2-(piperidin-1-yl)ethyl]amino}-5,8-dihydroxy-anthracene-9,10-dione (HAQ145)

The method follows that of HAQ105 using 1,4-Difluoro-5,8-hydroxy-anthraquinone (50 mg, 0.181 mmol), 1-(2-aminoethyl)-piperidine (232 mg, 1.81 mmol), pyridine (1 mL), 30 min, 100° C. The product HAQ145 was afforded as a dark blue powder (31.7 mg, 35%). M.p. 219-221° C.; $\delta_H$(250 MHz; $CDCl_3$); 1.45-1.55 (m, 4H, 4×ring-H), 1.55-1.7 (m, 8H, 8×ring-H), 2.55 (m, 8H, 2×$NCH_2H_2$), 2.65 (t, 4H, 2×$HNCH_2CH_2N$), 3.55 (q, 4H, 2×$HNCH_2CH_2N$), 7.05 (s, 2H, C(2)H and C(3)H), 7.15 (s, 2H, C(6)H and C(7)H), 10.5 (t, 2H, C(1)NH and C(4)NH), and 13.65 (s, 2H, C(5)OH, C(8)OH); $\delta_C$(62.9 MHz; $CDCl_3$; 24.37, 26.09, 40.72, 54.64, 57.63, 109.21, 115.48, 123.63, 124.63, 146.31, 155.46, and 185.35; FAB MS, m/z$(M+H)^+$ 493; Anal. calcd for $C_{28}H_{36}N_4O_6 \cdot 1.5H_2O$: C, 64.66; H, 7.27; N, 10.78. Found: C, 64.70; H, 7.55; N, 10.67.

Comparative Example 2

1-{[(2-Dimethylamino)ethyl]amino}-4-{[2-(piperidin-1-yl)ethyl]amino}-5,8-dihydroxyanthracene-9,10-dione (HAQ148)

The method follows that of HAQ105 using HAQ107 (62 mg, 0.18 mmol), 1-(2-aminoethyl)-piperidine (250 mg, 1.953 mmol), pyridine (1 mL), 30 min, 100° C. The product HAQ148 was afforded as a dark blue powder (42.9 mg, 65%). M.p. 220-223° C.; $\delta_H$(250 MHz; $CDCl_3$); 1.45-1.7 (m, 6H, 6×ring-H), 2.35 (s, 6H, 2×$NCH_3$), 2.55 (m, 4H, 2×$NCH_2CH_2$), 2.75 (2×t, 4H, 2×$HNCH_2CH_2N$), 3.5(q, 4H, 2×$HNCH_2CH_2N$), 7.05 (s, 2H, C(2)H and C(3)H), 7.1 (m, 2H, C(6)H and C(7)H), 10.45 (t, 2H, C(1)NH and C(4)NH), and 13.55 (s, 2H, C(5)OH, C(8)OH); $\delta_C$(62.9 MHz; $CDCl_3$); 24.28, 25.93, 40.51, 41.24, 45.63, 54.62, 57.50, 58.39, 109.23, 115.41, 123.73, 123.99, 124.75, 146.24, 155.44, and 185.41; FAB MS, m/z$(M+H)^+$ 453.

Biological Evaluation

Cytotoxicity of Substituted pyrollidinyl- and piperidinyl-alkylaminoanthraquinones Table 1 compares the activity of compounds possessing a side chain hydroxyl moiety (HAQ71, HAQ73, HAQ111) with HAQ148 and shows that the hydroxyl group is essential to the nM activity of these piperidinyl/pyrollidinyl substituted alkylaminoanthraquinones (see Table 1).

The non-symmetrically substituted compounds (HAQ71, HAQ73, HAQ110, HAQ111, HAQ121 and CAQ75) have similar potencies against the A2780 wildtype cell line.

Substitution of OH with Cl (compare HAQ71 with CAQ75) results in a >10-fold decrease in cytotoxicity although the enhanced activity against the resistant cells is still maintained for CAQ75 (RF=0.4). Furthermore CAQ75 was shown to be a significantly more potent in the A2780 cell line than the symmetrical chloropropyl congener CAQ74, which further emphasises the importance of the non-symmetrical substitution of these 1,4-disubstituted alkylaminoanthraquinones.

The chloromethyl piperidinyl and pyrollidinyl 1,4 disubstituted alkylaminoanthraquinones showed low cross resistance in a doxorubicin resistant (2780AD) and cisplatin resistant (A2780/cp70) ovarian carcinoma cell lines (Table 2). Hydroxyl and chloro substituted compounds show significant antitumour activity in human xenografted ovarian cancers in vivo in mice (Table 3).

In vivo Studies

Compound HAQ71, with the lowest RF (0.2) of the panel of compounds tested against the cisplatin resistant cells and its chloropropyl-substituted analogue, was selected for in vivo investigation in mice using tumour A2780 and A2780/cp70 cells grown as xenografts in mice. Significant anticancer activity in vivo of HAQ71 and CAQ75 was shown; both compounds exerting similar tumour growth delay in human xenografted wild-type and acquired cisplatin resistant tumours (A2780/cp70). The latter is very refractory to cisplatin and other covalent binding agents and has been characterised with elevated levels of glutathione, alterations in drug uptake/efflux and DNA repair mechanisms including mismatch repair deficiency.

Cytotoxicity in vitro of Di-N-oxides of aminoanthraquinones and chloroalkylaminoanthraquinones The cytotoxicity of the novel di-N-oxides of CAQs and non-covalent binding aminoanthraquinones was investigated in the ovarian carcinoma wild type cell line A2780, and the adriamycin resistant 2780AD and cisplatin resistant 2780CP cell lines.

All di-N-oxides were considerably less cytotoxic than their parent cytotoxic agents with $IC_{50}$ values in the μM range. The order of cytotoxicity of all agents tested was HAQ132N (>100 μm)<CAQ179N (46 μM)<CAQ181MN (38 μM)<CAQ167MN (36 μM)<CAQ192MN (8 μM). The cytotoxicity ratio (CR=$IC_{50}$ of alkylaminoanthraquinone-di-N-oxide/$IC_{50}$ alkylaminoanthraquinone) was used to calculate relative activities. Three di-N-oxides, HAQ132N, CAQ181MN and CAQ167MN, were more than 1000-fold less cytotoxic than their amine counterparts in the A2780 cell line. The CAQs were approx. 40-100 fold less cytotoxic than their amine counterparts. The order of CR was found to be AQ4N (17,000)>>HAQ132N (1,450)>>CAQ181MN (1293)>CAQ179N (80)>CAQ167MN (4167)>CAQ192MN (44).

N-oxides of selected compounds had very low cytotoxicity (Table 4) and have potential as bioreductive prodrugs.

TABLE 1

Inhibition of cell growth (IC50, nM) by 1,4-disubstituted aminoanthraquinones

| Compound | A2780 |
|---|---|
| HAQ71 | 8.4 |
| HAQ73 | 10.8 |
| HAQ111 | 6.1 |
| HAQ148 | >1,000 |

TABLE 2

Inhibition of cell growth by 1,4-disubstituted aminoanthraquinones

| Anthraquinone | A2780 nM | 2780AD nM | RF | A2780/cp70 nM | RF |
|---|---|---|---|---|---|
| HAQ163 | >1,000 | >1,000 | — | >1,000 | — |
| HAQ148 | >1,000 | >1,000 | — | >1,000 | — |
| CAQ191M | >1,000 | >1,000 | — | >1,000 | — |
| CAQ177M | 428 | 782 | 1.8 | 442 | 1 |
| CAQ190M | 178 | >1,000 | — | >1,000 | — |
| CAQ187M | 24 | 106 | 4.4 | 357 | 14.9 |
| CAQ183M | 40 | 91 | 2.3 | 69 | 1.7 |
| CAQ176M | 29 | 292 | 10.1 | 79 | 2.7 |
| CAQ166M | 9 | 75 | 8.3 | 63 | 7 |
| CAQ188M | 68 | 342 | 5.0 | 96 | 1.4 |
| CAQ172 | 576 | 426 | 0.7 | 535 | 0.9 |
| CAQ74 | >1,000 | >1,000 | — | >1,000 | — |

HAQ = hydroxy deriv;
CAQ = chloro deriv;
M = mustard
All compounds are R and S mixtures unless otherwise stated.
All compounds are mixed side chains (non-symmetrical) unless otherwise stated
$IC_{50}$ is the concentration of drug (nM) required to inhibit cell growth by 50%.
A2780 is the wild type ovarian cell line; A2780/cp70 cisplatin and 2780AD adriamycin resistant variants.
RF = resistance factor ($IC_{50}$ in resistant cell line/$IC_{50}$ in parent cell line).

TABLE 3

Effect of compound HAQ71 and CAQ75 on doubling time (days) of a human ovarian tumour xenograft (A2780) and a cisplatin resistant variant (A2780/cp70).

| tumour | Untreated | HAQ71 | CAQ75 |
|---|---|---|---|
| A2780 | 2.94 ± 0.34 | 5.23 ± 0.39 (177%) | 5.83 ± 0.40 (198%) |
| A2780/cp70 | 2.52 ± 0.17 | 4.33 ± 0.16 (172%) | 4.18 ± 0.27 (166%) |

HAQ = hydroxy deriv;
CAQ = chloro deriv
( ) = percent increase in median life span - calculated as time taken for tumour to reach twice its initial volume.
Compound HAQ71 dosed at 20 mg/kg and compound CAQ75 at 16 mg/kg both i.p.

TABLE 4

Growth Inhibition ($IC_{50}$) of Di-N-oxides of Aminoanthraquinones and Chloroalkylaminoanthraquinones Against Ovarian Cancer Cell Line

| Compound | A2780 [nM] |
|---|---|
| HAQ110 | 69 |
| HAQ132N CR | >100,000 >1,449 |
| CAQ172 | 5.765e+09 |
| CAQ179N CR | |

TABLE 4-continued

Growth Inhibition ($IC_{50}$) of Di-N-oxides of Aminoanthraquinones and Chloroalkylaminoanthraquinones Against Ovarian Cancer Cell Line

| Compound | A2780 [nM] |
|---|---|
| CAQ166M | 9.357e+09 |
| CAQ167MN CR | |
| CAQ176M | 2.938e+10 |
| CAQ181MN CR | |
| CAQ190M | 178790044 |
| CAQ192MN CR | |
| AQ4 | 6 |
| AQ4N | >100,000 |
| CR | >16,667 |

HAQ = hydroxy deriv;
CAQ = chloro deriv;
N = N-oxide;
M = mustard;
MN = N-oxide of mustard
CR = cytotoxicity ratio ($IC_{50}$ of amine/$IC_{50}$ of N-oxide).

The invention claimed is:

1. An anthraquinone compound of the general formula I or a salt thereof

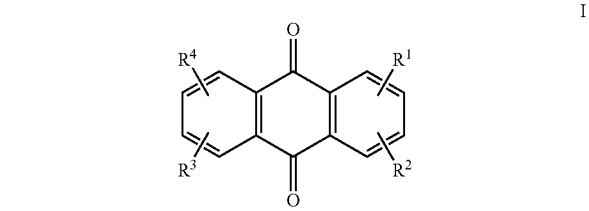

in which $R^1$ is at the 4 position and is selected from the group consisting of H, —$NHR^ON (R^5)_2$ in which $R^O$ is a $C_{1-12}$ alkanediyl and each $R^5$ is H or optionally substituted $C_{1-4}$ alkyl, and a group of formula II

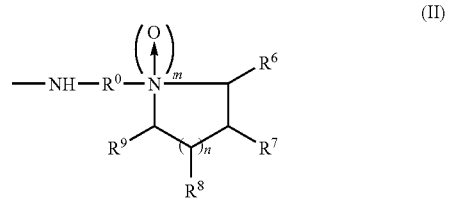

in which at least one of $R^6$, $R^7$ and $R^8$ is selected from $X^2$, and $X^2$ substituted $C_{1-4}$ alkyl and any others are H or $C_{1-4}$ alkyl; $R^9$ is selected from H, $C_{1-4}$ alkyl, $X^2$ and $X^2$ substituted $C_{1-4}$ alkyl;

m is 0 or 1;

n is 1 or 2;

$R^2$ is at the 1 position and is selected from H, —$NHR^ON (R^5)_2$ in which $R^O$ is a $C_{1-12}$ alkanediyl and each $R^5$ is H or optionally substituted $C_{1-4}$ alkyl, and a group of formula II

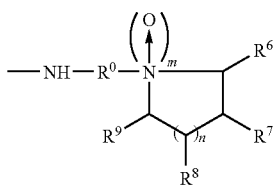

in which at least one of $R^6$, $R^7$ and $R^8$ is selected from $X^2$, and $X^2$ substituted $C_{1-4}$ alkyl and any others are H or $C_{1-4}$ alkyl; $R^9$ is selected from H, $C_{1-4}$ alkyl, $X^2$ and $X^2$ substituted $C_{1-4}$ alkyl;

m is 0 or 1;

n is 1 or 2;

$R^3$ is at the 5 position and is H or OH;

$R^4$ is at the 8 position and is H or OH;

$X^2$ is a halogen atom, a hydroxyl group, an aryloxy group or an acyloxy group or another nucleofugal leaving group;

provided that at least one of $R^1$ or $R^2$ is a group of formula II.

2. A compound according to claim 1 in which $R^1$ and $R^2$ are each a group of formula II.

3. A compound according to claim 1 in which $R^1$ is a group of formula II and $R^2$ NHR$^0$N $(R^5)_2$.

4. A compound according to claim 3 in which each $R^5$ is the same and is H or $CH_3$.

5. A compound according to claim 1 in which $R^3$ and $R^4$ are both hydroxyl.

6. A compound according to claim 1 in which $R^3$ and $R^4$ are both H.

7. A compound according to claim 1, in which m is 1.

8. A compound according to claim 1, in which m is 0.

9. A compound according to claim 1, in which n is 2.

10. A compound according to claim 1, in which $X^2$ is a halogen atom or a nucleofugal leaving group.

11. A compound according to claim 10, in which $X^2$ is chlorine.

12. A compound according to claim 1, in which either
   i) $R^6$ is $CH_2X^3$ and $R^7$ is H; or
   ii) $R^6$ is H and $R^7$ is $X^3$.

13. A compound according to claim 12 in which $R^6$ is $CH_2X^3$ and $R^7$ is H.

14. A compound according to claim 13 in which n is 2 and $R^9$ $CH_2X^3$ in which $X^3$ is the same as $X^3$ in $R^6$.

15. A composition comprising a compound according to claim 7 and an excipient.

16. A composition according to claim 15 which is a pharmaceutical composition and in which the excipient is a pharmaceutically acceptable excipient.

17. A composition comprising a compound according to claim 10 and an excipient.

18. A compound selected from the group consisting of:
1-{[(2-Dimethylamino)ethyl]amino}-4-{[2-(3-hydroxypiperidin-1-yl)ethyl]amino}-anthracene-9,10-dione;
1,4-Bis-{[2-(3-hydroxypiperidin-1-yl)ethyl]-amino}-anthracene-9,10-dione;
1,4-Bis-{[2-(3-hydroxymethylpiperidine-1-yl)ethyl]amino}-5,8-dihydroxy-anthracene-9,10-dione;
1,4-Bis-{[2-(3-hydroxymethylpiperidine-1-yl)ethyl]amino}-anthracene-9,10-dione;
1-[(2-Dimethylamino)ethylamino]-4-[2-(3-hydroxymethyl-piperidin-1-yl)ethylamino]-5,8-dihydroxy-anthacene-9,10-dione;
1-[(2-Dimethylamino)ethylamino]-4-[2-(3-hydroxypiperidin-1-yl)-ethylamino]-5,8-dihydroxy-anthracene-9,10-dione;
1,4-Bis-{[2-(2-hydroxymethylpiperidin-1-yl)ethyl]amino}-5,8-dihydroxy-anthracene-9,10-dione;
1-{[(2-Dimethylamino)ethyl]amino}-4-{[2-(2-hydroxymethylpyrrolidin-1-yl)ethyl]amino}-5,8-dihydroxy-anthracene-9,10-dione;
1-{[(2-Dimethylamino)ethyl]amino}-4-{[2-(4-hydroxypiperidin-1-yl)ethyl]amino}-anthracene-9,10-dione;
1,4-Bis-{[2-(3-hydroxypyrrolidin-1-yl)ethyl]amino}-5,8-dihydroxy-anthracene-9,10-dione;
1,4-Bis-{[2-(4-hydroxypiperidin-1-yl)ethyl]amino}-5,8-dihydroxy-anthracene-9,10-dione;
1-{[(2-Dimethylamino)ethyl]amino}-4-{[2-(4-hydroxypyrrolidin-1-yl)ethyl]amino}-5,8-dihydroxy-anthracene-9,10-dione;
1-{[(2-Dimethylamino)ethyl]amino}-4-{[-2-(2-hydroxymethylpiperidin-1-yl)ethyl]amino}-5,8-dihydroxyanthracene-9,10-dione;
1,4-Bis-{[2-(2-hydroxymethylpyrrolidin-1-yl)ethyl]amino}-5,8-dihydroxy-anthracene-9,10-dione;
1-{[2-(2,6-Dihydroxymethylpiperidin-1-yl)ethyl]amino}-4-{[(2-Dimethylamino)ethyl]amino}-5,8-dihydroxyanthracene-9,10-dione; and 1-{[2-(2-Hydroxymethylpyrrolidin-1-yl)ethyl]amino}-anthracene-9,10-dione.

19. A compound selected from the group consisting of:
1-{[2-(3-Chloropiperidin-1-yl)ethyl]amino}-4-{[(2-dimethylamino)ethyl]amino}-5,8-dihydroxyanthracene-9,10-dione;
1-{[2-(4-Chloropiperidin-1-yl)ethyl]amino}-4-{[(2-dimethylamino)ethyl]amino}-5,8-dihydroxyanthracene-9,10-dione;
1-{[2-(2-Chloromethylpyrrolidin-1-yl)ethyl]-amino}-4-{[(2-Dimethylamino)ethyl]amino}-5,8-dihydroxyanthracene-9,10-dione;
1-{[2-(3-Chloropyrrolidin-1-yl)ethyl]amino}-4-{[(2-dimethylamino)ethyl]amino}-5,8-dihydroxyanthracene-9,10-dione;
1-{[2-(3-Chloropiperidin-1-yl)ethyl]amino}-4-{[(2-dimethylamino)ethyl]amino}-anthracene-9,10-dione;
1-{[2-(2-Chloromethylpiperidin-1-yl)ethyl]amino}-4-{[(2-dimethylamino)ethyl]amino}-5,8-dihydroxyanthracene-9,10-dione;
1-{[2-(2-Chloromethylpiperidin-1-yl)ethyl]-(amino)-4-{[(2-dimethylamino)ethyl]amino}-5,8-dihydroxyanthracene9,10-dione;
1-{[2-(2,6-Dichloromethylpiperidin-1-yl)ethyl]-amino}-4-{[(2-dimethylamino)ethyl]amino}-5,8-dihydroxyanthracene-9,10-dione; and
1-{[2-(2-chloromethylpyrrolidin-1-yl)ethyl]amino}-anthracene-9,10-dione.

20. A compound selected from the group consisting of:
1,4-Bis-{[2-(2-chloromethylpyrrolidin-1-yl)ethyl]amino}-5,8-dihydroxyanthracene-9,10-dione;
1,4-Bis-{[2-(3-chloromethylpiperidin-1-yl)ethyl]amino}-anthracene-9,10-dione;

1,4-Bis-{[2-(3-chloromethylpiperidin-1-yl)ethyl]amino}-5,8-dihydroxyanthracene-9,10-dione; and 1,4-Bis-{[2-(2-chloromethylpiperidin-1-yl)ethyl]amino}-5,8-dihydroxyanthracene-9,10-dione.

21. The compound:

1-{[2-(2-Hydroxymethylpyrrolidin-1-yl-N-oxide)ethyl]amino}-4-{[(2-dimethylamino-N-oxide)ethyl]amino}-5,8-dihydroxy-anthracene-9,10-dione.

22. A compound selected from the group consisting of:

1-{[2-(3-Chloropiperidin-1-yl-N-oxide)ethyl]amino}-4-{[(2-dimethylamino-N-oxide)ethyl]amino}-5,8-dihydroxyanthracene-9,10-dione;

1-{[2-(4-Chloropiperidin-1-yl-N-oxide)ethyl]amino}-4-{[(2-dimethylamino-N-oxide)ethyl]amino}-5,8-dihydroxyanthracene-9,10-dione; and 1-{[2-(2-Chloromethylpyrrolidin-1-yl-N-oxide)ethyl]amino}-4-{[(2-dimethylamino-N-oxide)ethyl]amino}-5,8-dihydroxyanthracene-9,10-dione.

23. The compound:

1,4-Bis-{[2-(2-chloromethylpiperidin-1-yl-N-oxide)ethyl]amino}-5,8-dihydroxyanthracene-9,10-dione.

24. A composition comprising a compound and an excipient, wherein the compound is according to claim 8.

\* \* \* \* \*